(12) United States Patent
Ameri

(10) Patent No.: US 7,384,147 B1
(45) Date of Patent: Jun. 10, 2008

(54) APPARATUS AND METHOD FOR OPHTHALMOMETERY

(76) Inventor: Hossein Ameri, 321 N. Monterey St., Apt. #8, Alhambra, CA (US) 91801

( * ) Notice: Subject to any disclaimer, the term of this patent is extended or adjusted under 35 U.S.C. 154(b) by 192 days.

(21) Appl. No.: 11/494,806

(22) Filed: Jul. 28, 2006

(51) Int. Cl.
*A61B 3/00* (2006.01)
*A66B 3/10* (2006.01)
(52) U.S. Cl. .................. 351/245; 351/200; 351/204
(58) Field of Classification Search ............ 351/200, 351/204, 245
See application file for complete search history.

(56) References Cited

U.S. PATENT DOCUMENTS

| 2,622,439 | A | | 12/1952 | Copper | |
|---|---|---|---|---|---|
| 2,677,894 | A | * | 5/1954 | Belgard | ............... 33/200 |
| 5,379,079 | A | | 1/1995 | Kratky | |
| 7,322,697 | B2 | * | 1/2008 | Jojiki | ............... 351/204 |
| 2006/0077342 | A1 | * | 4/2006 | Fischer | ............... 351/204 |

FOREIGN PATENT DOCUMENTS

GB          655787        8/1951

OTHER PUBLICATIONS

Lasiris Collimated Line Heads; Collimated Line Generators for Variable Working Distance; StockerYale; http://lasers.stockeryale.com.
Baumer electronic; Distance measuring sensors: Baumer Electronic, Ltd.; www.baumerelectric.com; Aug. 2002.
Leslie C. Drews, M.D.; Exophthlamometry and a new Exophthalmometer; Trans Am Ophthalmol Soc. 1956; 54:215-252.
Hossein Ameri et al., Comparison of unilateral and simultaneous bilateral measurement fo the globe position, using the hertel; Ophtal Plast Reconstr Surg, vol. 20, No. 6, 2004.
Davanger M. Principles and sources or error in exophthalmometry. A new exophthalmometer. Acta Ophthalmol. 1970; 48:625.
Musch D. The reliability of hertel exophthalmometry; observer variation between physcian and layer reader. Opthalmology. 1985;92:1177-1180.
Digital Caliper; http://www.wihatools.com/411serie_calipers.htm. www.guldenophthalmics.com/pages/product_pages/luedde.html.
Banner sensor products 2005 by Banner Engineering Corp.; www.bannerengineering.com.

* cited by examiner

*Primary Examiner*—Huy K Mai
(74) *Attorney, Agent, or Firm*—Peter Ganjian

(57) ABSTRACT

A universal frame for providing a hands free, stable base for ophthalmic measurements comprising a first adjustable ear piece and a second adjustable ear piece, and a measuring instrument detachably connected with the universal frame for exopthalmos and enopthalmos measurements.

30 Claims, 16 Drawing Sheets

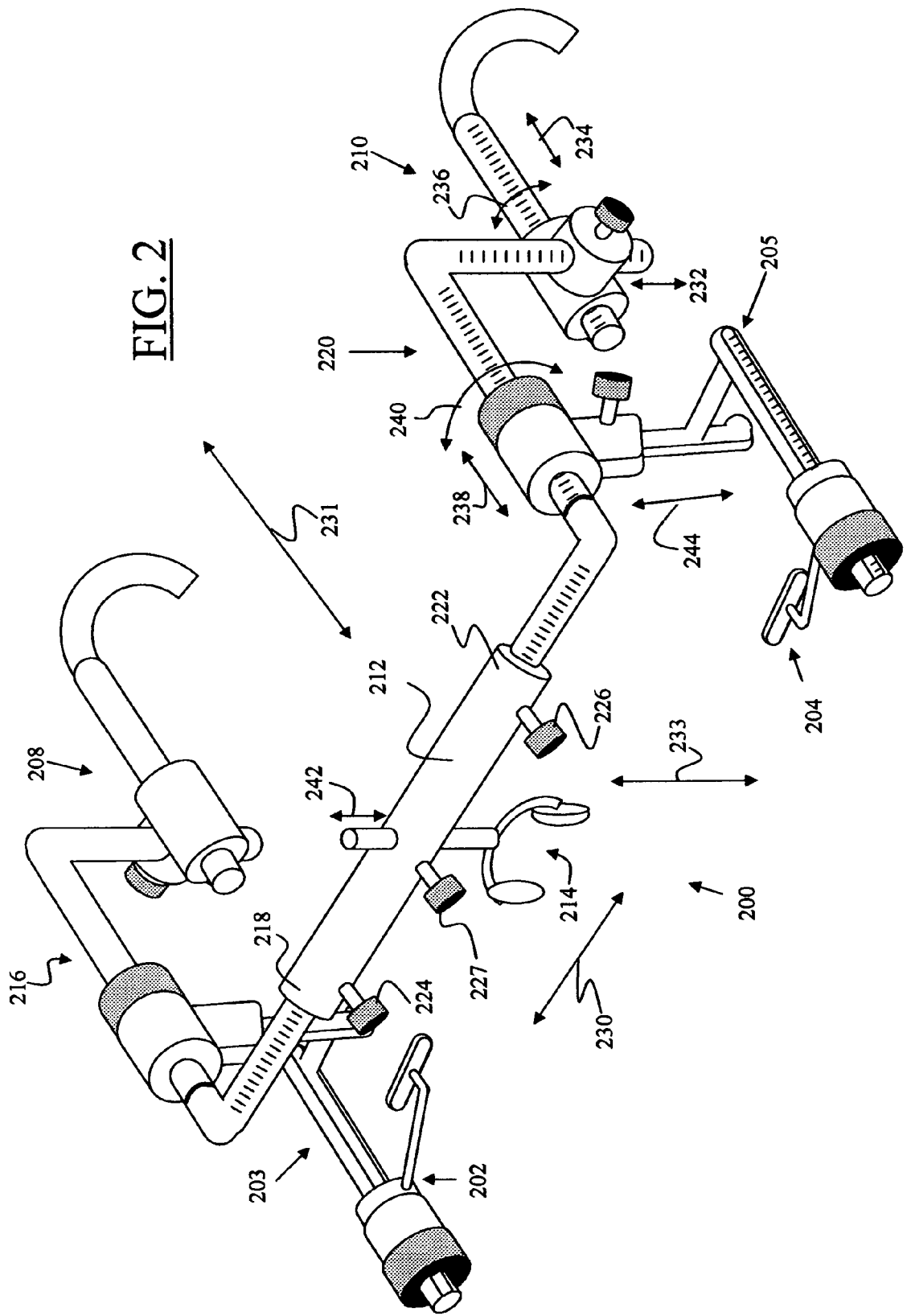

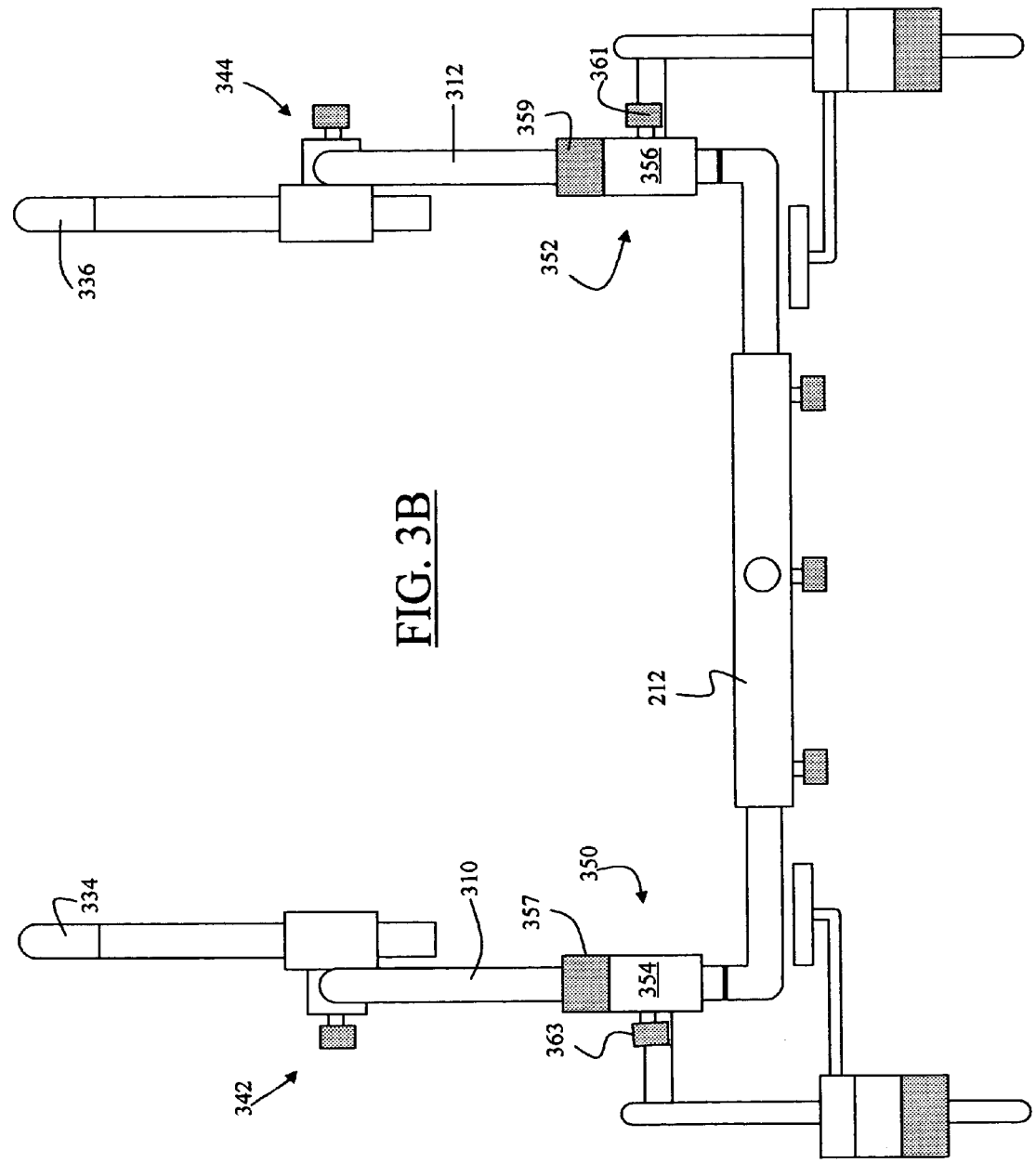

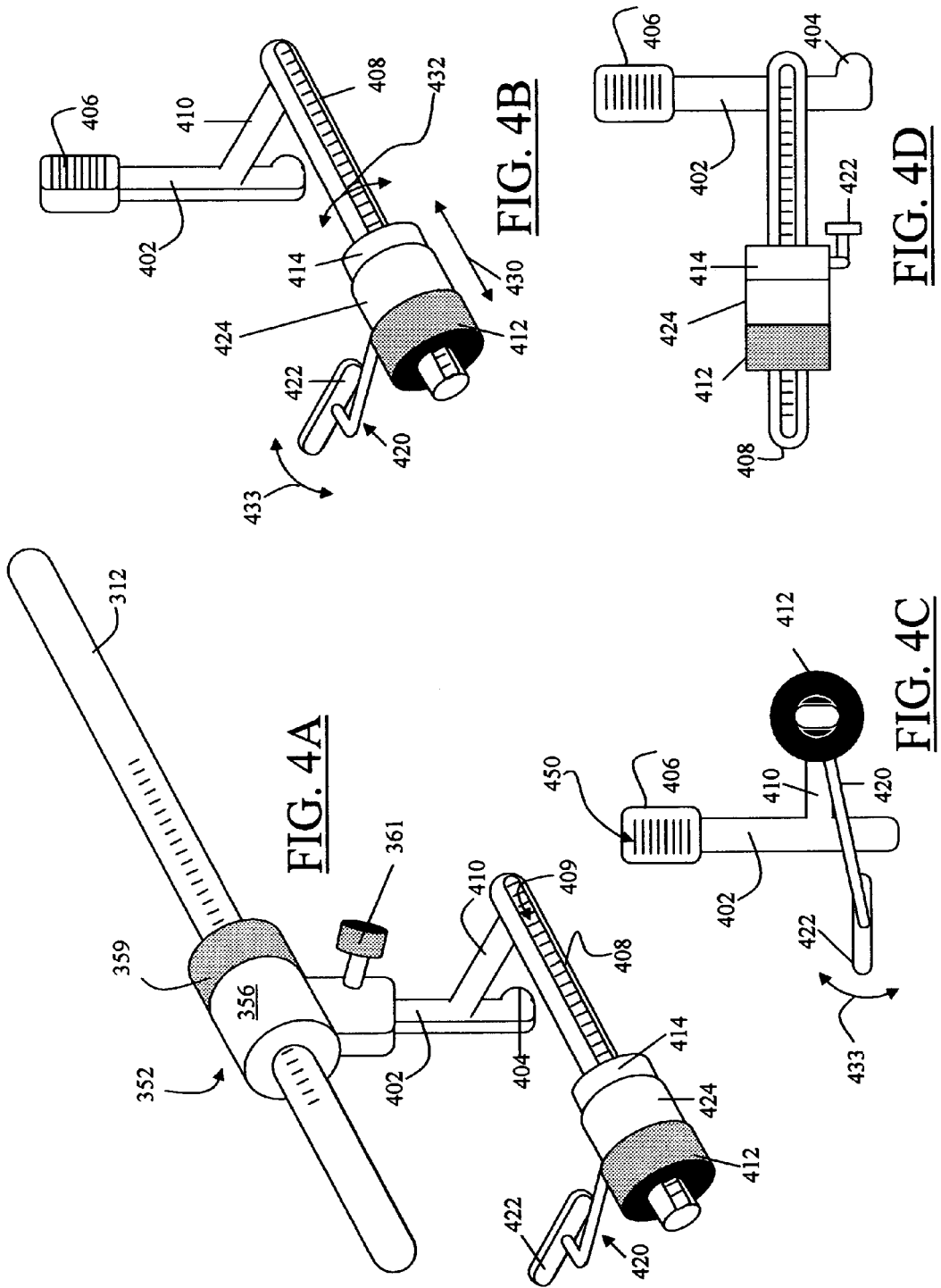

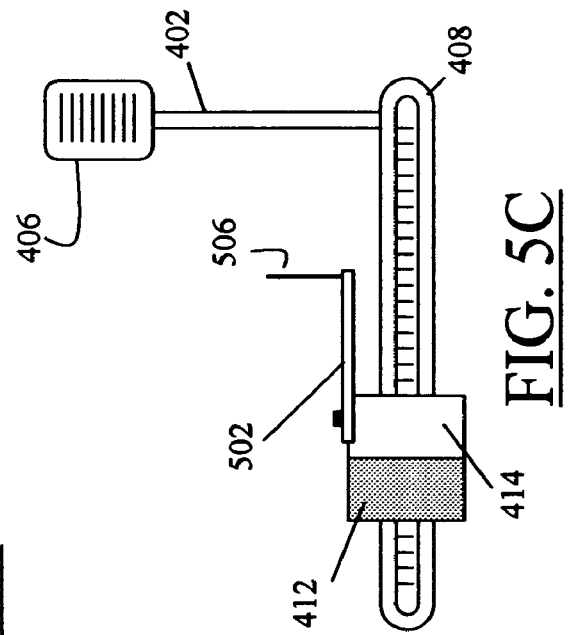
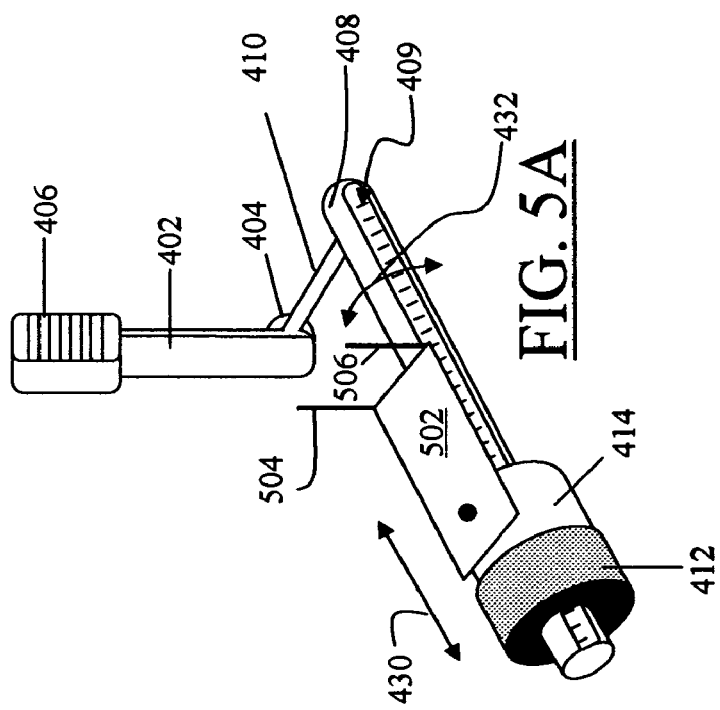
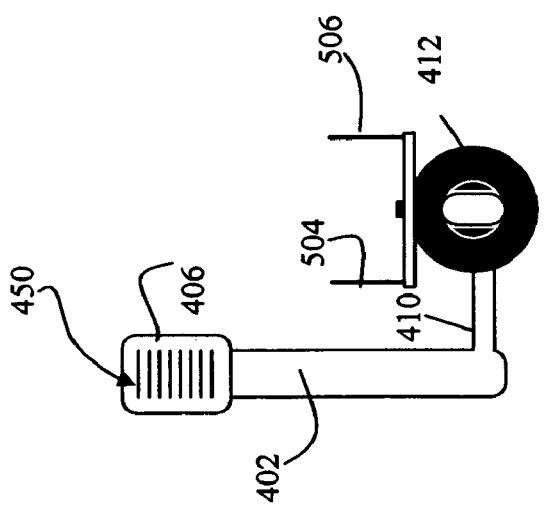

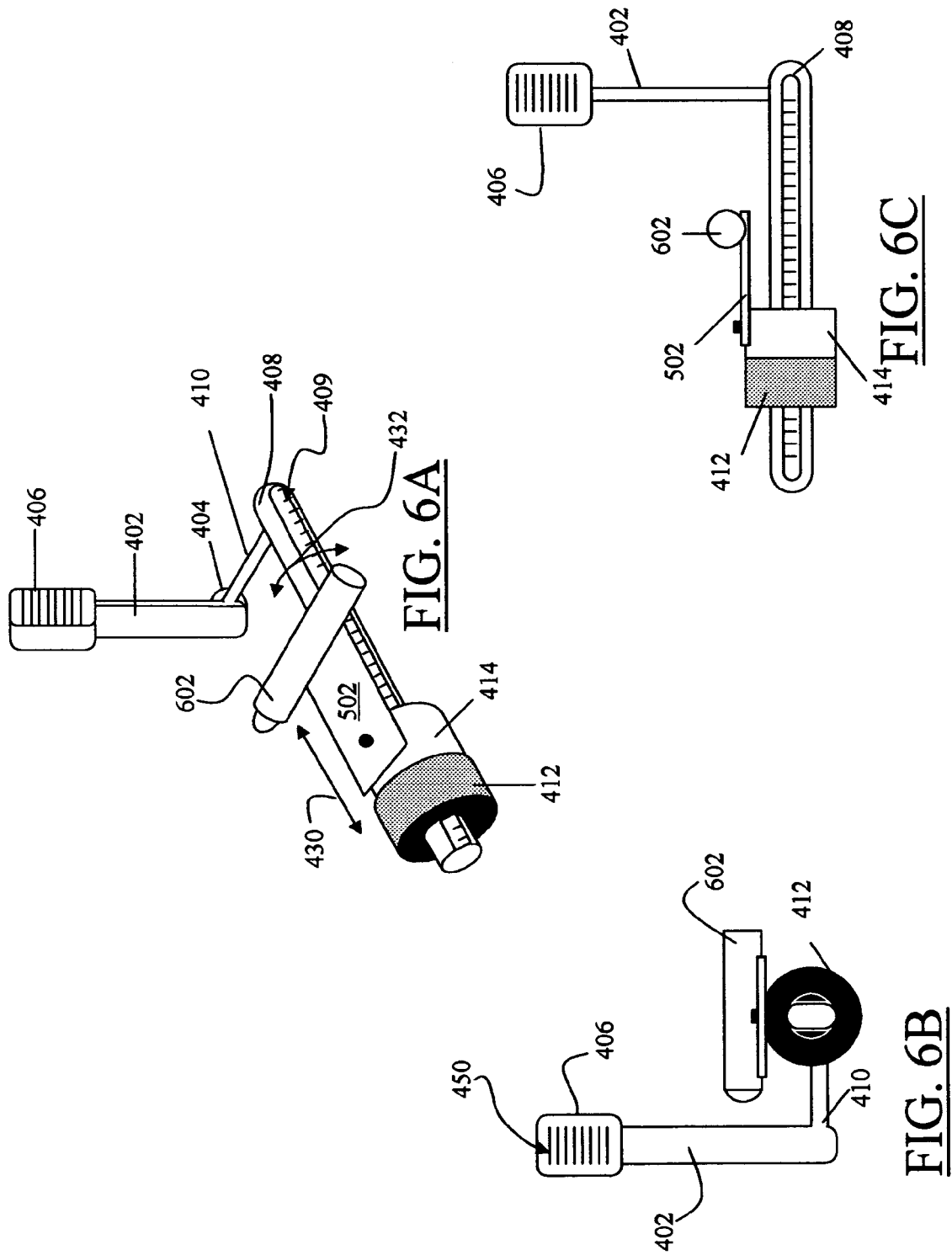

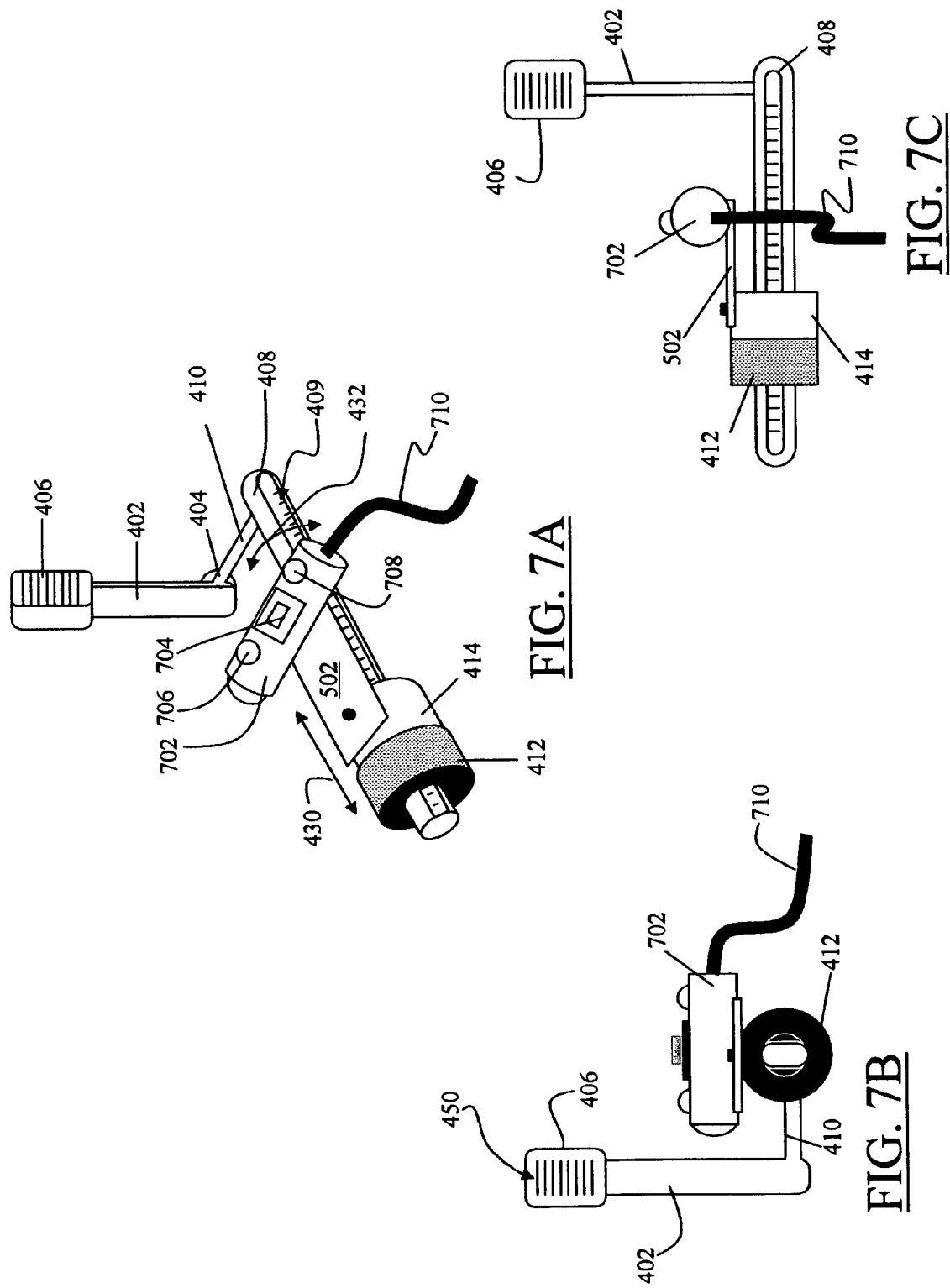

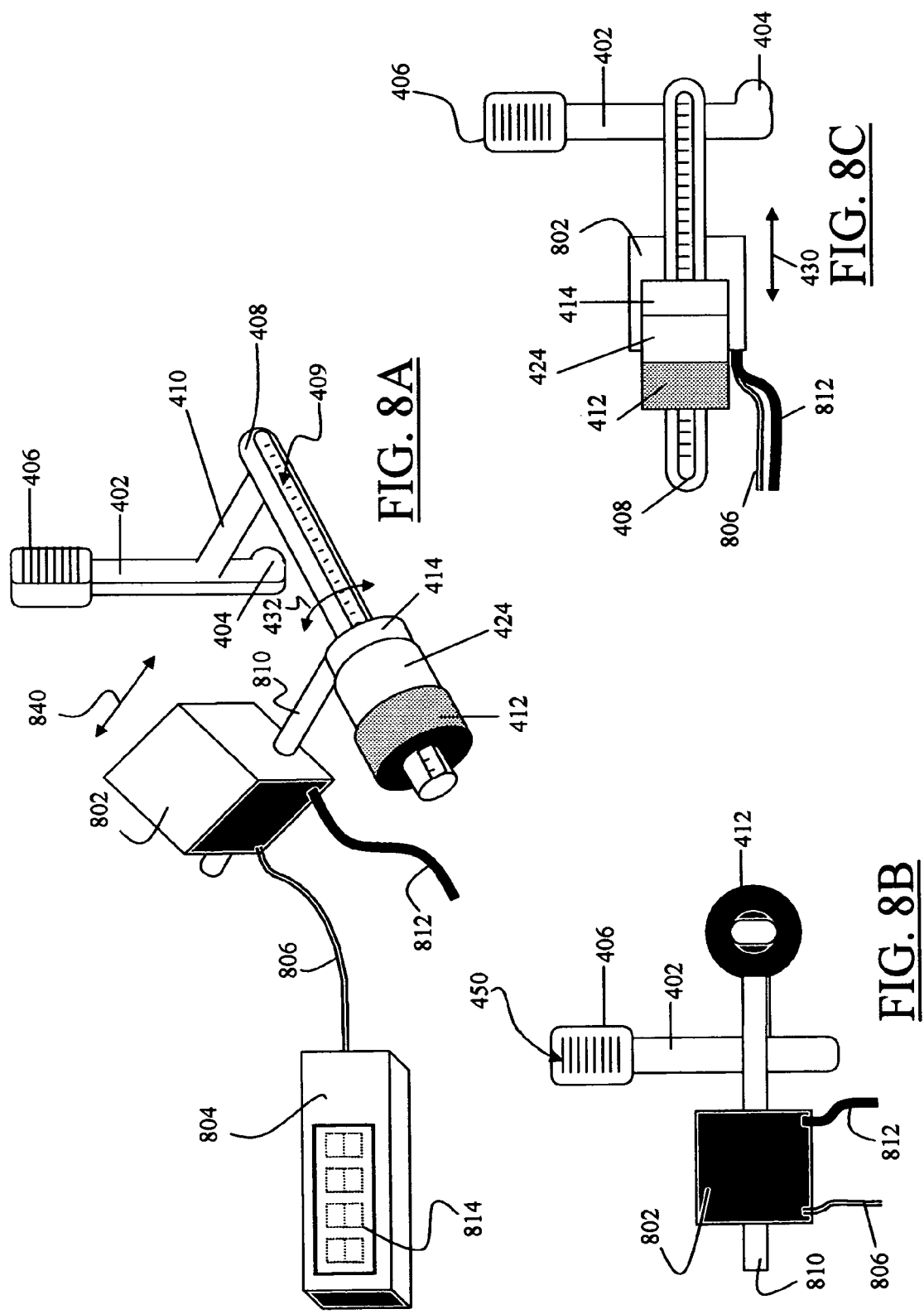

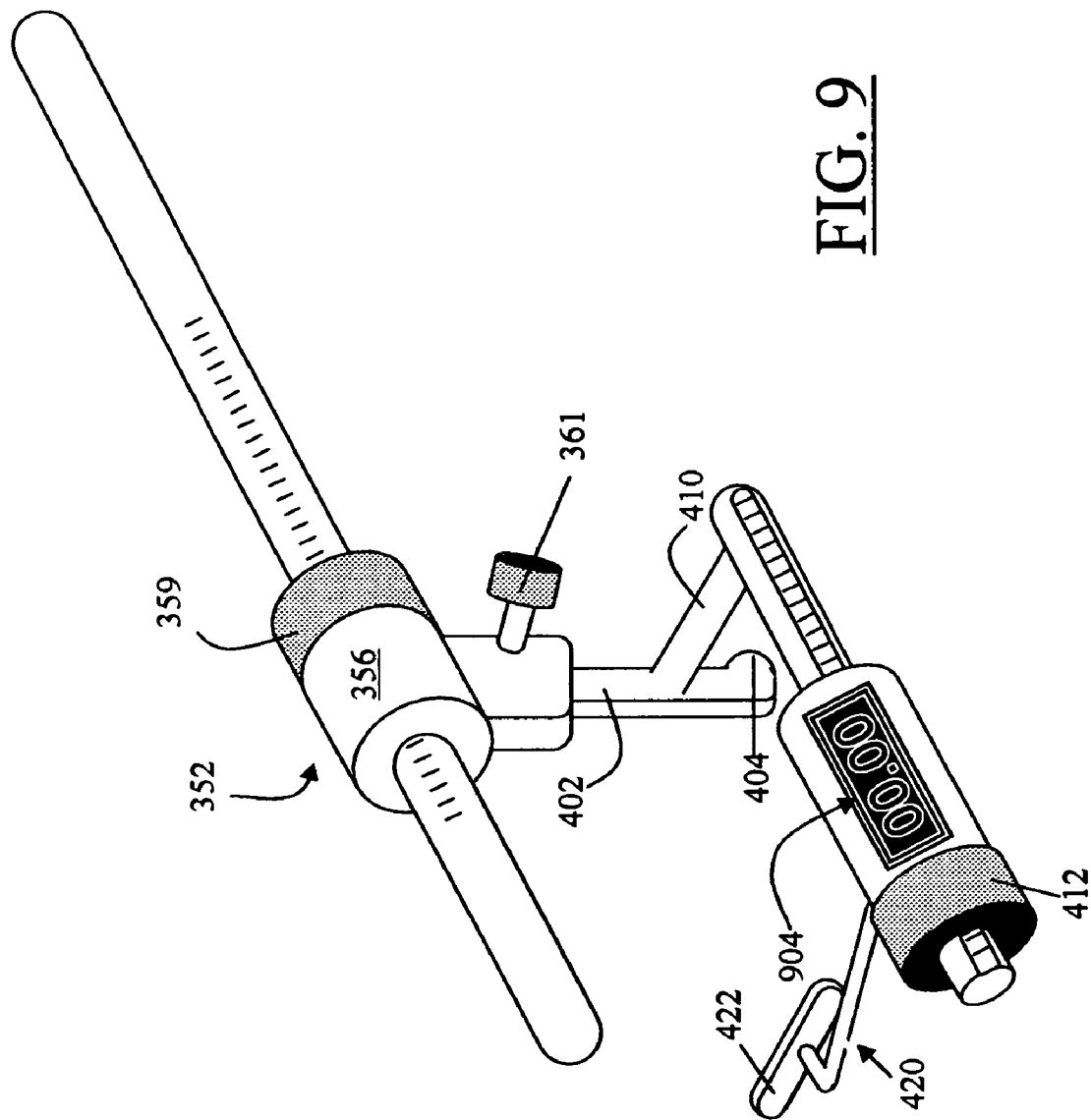

APPARATUS AND METHOD FOR OPHTHALMOMETERY

BACKGROUND OF THE INVENTION (1) Field of the Invention

This invention is related to an instrument used in the field of opthalmology and plastic surgery and, more particularly, it relates to ophthalmic instruments that are used for measuring the exopthalmos and the enopthalmos of the eyes.

(2) Description of Related Art

As the prior art FIG. 1A illustrates, the eyeball 100 is located in a boney socket (the eye socket) 102 that protects the eyeball 100 from trauma. The space inside the eye socket 102 is generally known as the "orbit," which contains fat and connective tissues that support the eyeball 100 and its external attachments such as vessels, nerves, muscles, etc. Exopthalmos (or "proptosis") is the abnormal protrusion of the eyeball 100 from the orbit (anterior displacement) due to exopthalmogenic diseases that cause the swelling of the orbital content, resulting in the protrusion of the eyeball 100 out of the eye socket 102. Enopthalmos is the backward (or posterior) displacement of the eyeball 100 into the orbit, which may be caused by, for example, fracture of the eye socket 102.

Opthalmometers are used extensively to measure the amount of exophthalmia and enophthalmia in patients. Opthalmometry of the eyeball position in the orbit facilitates the diagnosis of exophthalmic and or enophthalmic conditions within patients, which is particularly important for patients having orbital disease that can cause exopthalmogenic or enopthalmogenic conditions. For example, progression of the proptosis in a patient with dysthyroid eye disease could be a sign of activity of the disease and may indicate urgent treatment, while, in the stable phase of the disease accurate measurement of the amount of proptosis is important in making the decision for surgery and planning for the amount of correction.

In general, the eyeball position along the anterior-posterior axis of the eyeball is measured by the distance (or orbital distance) 104 between the lateral orbital rim 106 (the outer edge (or the profile) of the eye socket 102) and the corneal apex 108 (the front surface of the eyeball 100). That is, the distance 104 is measured from the lateral orbital rim 106 to a vertical frontal facial plane 109, which is tangent to the corneal apex 108 and perpendicular to the anterior-posterior axis. It should be noted that although the superior orbital rim (not shown) has also been used as a reference point for opthalmometric measurements (e.g., U.S. Pat. No. 5,379,079 to Kratky), it is generally not as reliable of a reference point for opthalmometric measurements compared to the use of lateral orbital rim 106.

There are generally three types of opthalmometric measurements, including absolute, comparative, and relative opthalmometry. The absolute opthalmometry measures the degrees of exophthalmia and or the enophthalmia, and compares this measurement with a known normal value (e.g., an average on a chart). The comparative opthalmometry measures the exopthalmos and or the enopthalmos, but compares the resulting measurements with a previously taken set of measurements in the same eye. In relative opthalmometry the exopthalmos and or the enopthalmos measurements of the right and the left eyes are compared with each other.

As is illustrated in the prior art FIG. 1B, it is possible to perform opthalmometry to determine the exopthalmos and or the enopthalmos by using an ordinary transparent ruler 110. The base of the rule 110 is placed on the margin of the lateral orbital rim 106 and the corneal apex 108 is visualized through the transparent ruler (with the eye of the patient looking straight ahead), then a reading of the measurement is taken. However, if the ruler 110 is tilted to any one of the sides indicated by the directional arrows 112 or the examiner moves or the line of sight of the examiner is not exactly perpendicular to the ruler 110, the readings of the measured displacement of the eyeball 100 (the orbital distance 104) would not be accurate. This produces an error commonly known as the parallax error, which is the apparent displacement, or difference in the apparent position of the eyeball, caused by actual change (or difference) of position of the point of observation (by the examiner).

One of the most widely used opthalmometric instruments is the HERTEL exopthalmometer, which is used to measure the eyeball position. The HERTEL exopthalmometer is composed of two mirrors at each side that overlap the image of the corneal apex on the image of a scale and allows the examiner to perform the measurements while standing in front of the patient. It is a binocular instrument that rests on each lateral orbital rim and allows an observer in front, with the aid of the mirrors, to view images of the corneal apex of the two eyes as seen in profile, superimposed upon a millimeter scale. A measurement is obtained of the relative distance of the apex of the cornea from a zero reference point, i.e., an imaginary horizontal line in a plane parallel to the front of the patient's face uniting the lateral orbital rims.

Large footplates (or bases) and lack of a mechanism to ensure proper resting of the footplates on the lateral orbital rims makes the HERTEL exopthalmometer prone to error in measuring the eyeball position. As examiner's both hands are engaged, holding the instrument next to the patient's face, it is generally not possible to ensure that HERTEL exopthalmometer footplates are resting properly on the lateral orbital rims on each side. Further more, even if the footplates are properly rested on the lateral orbital rims, there is no mechanism to ensure that they are placed symmetrically at equidistance from each orbital rim. When the HERTEL exopthalmometer is parallel to the coronal plane but is displaced to the left or right, asymmetrical placement of the footplate will result in under-reading in both sides as the medially displaced footplate does not sit properly on the lateral orbital rim. However, if the instrument is not parallel to the coronal plane the result would be under-reading of the medially displaced side only, and the reading of the other side will depend on the direction of the rotation of the instrument at horizontal plane.

Freedom of rotation along the horizontal plane (joining the right and the left lateral orbital rims) is another source of opthalmometric errors when using the HERTEL exopthalmometer. The horizontal rotation of the instrument can occur when the examiner applies less pressure on the left or the right lateral orbital rim to rest the footplates of the HERTEL exopthalmometer, especially if either one of the lateral orbital rims is tender, are asymmetrical, or have asymmetric swelling of soft tissues, or are fractured. The rotation at horizontal plane results in under-reading of the side that HERTEL exopthalmometer is rotated towards, and over-reading of the other side.

It has been found that parallax errors are eliminated when the distance between the lateral orbital rim and the anterior-posterior position of the eyeball (the orbital distance) is approximately about 20 mm. However, when this distance differs, it has been found that the images of the corneal apex and the ruler overlap properly only when the sighting line of the examiner is at the right angle to the frontal plane. In other words, movement of the examiner to the right or left, while looking at the image of the apex of the cornea, introduces parallax error. Given the fact that the above distance varies among different people and considering the practical difficulties of proper placing of the footplates, which can increase or decrease the distance between the footplate and the anterior-posterior axis of the eyeball, there is a considerable chance of parallax error with HERTEL exopthalmometer.

Leudde exopthalmometer (illustrated in the prior art FIG. 1C) is another less widely used opthalmometric instrument. Leudde exopthalmometer is a thick transparent (rectangular-cube) ruler that has two exactly similar scales on two opposing sides, along the length of the rectangular-cube. When Leudde exopthalmometer is placed over the lateral orbital margin, the examiner must view the anterior-posterior positional axis of the eyeball by overlapping the two scales in each side of the instrument by moving to the left or right of the instrument so that the scales on either side overlap and look as a single scale. This way, the line of sighting of the examiner would become perpendicular to the instrument. Regrettably, any inward or outward (lateral movement), or any type of tilting of the instrument would cause parallax error.

The Naugle exopthalmometer is yet another opthalmometer that is similar to the HERTEL exopthalmometer, but it uses the superior and inferior orbital rims for measuring the anterior-posterior positional axis of the eyeball, instead of the lateral orbital rim. In addition, the Naugle exopthalmometer may also be used for measuring most vertical deviations of the eyeball. Although the superior and inferior orbital rims have been used by a few other researchers, studies have shown that they are more asymmetrical and less reliable than lateral orbital rims as reference point for measurement. However, the Naugle exopthalmometer is superior to HERTEL in fractures of orbit that involve lateral orbital rim and in cases for patients that have had surgical removal of the lateral orbital rim.

The British patent 655,787 to Copper discloses an opthalmometric instrument that is used for measuring the resistance encountered in forcing the eyeball back into the orbit or eye socket, with such resistance affording the oculist data concerning the consistency and other qualities of the intraorbital tissues. The opthalmometric instrument taught by Copper also enables measurement of exopthalmos or protrusion of the eye along the anterior-posterior axial displacement of the eyeball.

The Copper instrument includes two metal strays 3 of seemingly equal length at a right and a left side of the instrument, that couple with a headband at one end (proximal to the eye), and a flat metal strip cross bar 1 at the other end (distal from the eye). The proximal ends of the strays 3 coupled with the headband rest on the right and the left orbital rims, simultaneously, while the distal ends thereof are coupled with the cross bar 1 via a set of nuts 5. The cross bar 1 and the metal strays 3 form a "frame" for the patient to be worn during examination. The use of headband to secure the instrument on a patient's face while the measuring instrument (dynamometer) touches the eyeball is not practical in that the headband itself may slip, tilt, move, or not be placed or oriented properly, causing a possible injury to the eye during examination. Further, the use of seemingly equal length metal strays 3 will result in erroneous measurement of the degree of exopthalmos on patients with asymmetrical lateral orbital rims.

Unfortunately, present constructions of instruments do not provide a particularly accurate opthalmometric measurements (or readings) in that they depend on the position of the person using the instrument (the examiner), and indeed, any slight movement of the examiner, the patient, or the instrument itself can lead to incorrect and unsafe examination of the eyes. Therefore, in light of the current state of the art and the drawbacks to current instruments mentioned above, a need exists for an apparatus and a method that would mitigate these problems. In particular, a need exists for an apparatus and a method that would provide a stable base or frame for opthalmometric measurements, obviate parallax errors, and be safe to use.

BRIEF SUMMARY OF THE INVENTION

One aspect of the present invention provides an apparatus, comprising:
  a universal frame for providing a hands free, stable base for ophthalmic measurements comprising a first adjustable ear piece and a second adjustable ear piece; and
  a measuring instrument detachably connected with the universal frame for exopthalmos and enopthalmos measurements.

One optional aspect of the present invention provides an apparatus, wherein:
  the universal frame is comprised of:
    an adjustable front bar having an adjustable nose piece;
    a first side bar coupled with a first end of the adjustable front bar, and terminating in the first adjustable ear piece;
    a second side bar coupled with a second end of the adjustable front bar, and terminating in the second adjustable ear piece.

Another optional aspect of the present invention provides an apparatus, wherein:
  the adjustable front bar includes a front bar adjuster for varying a width of the universal frame parallel along a frontal facial plane.

Yet another optional aspect of the present invention provides an apparatus, wherein:
  the front bar adjuster is comprised of:
    a first front bar adjuster that is proximal to the first end of the adjustable front bar; and
    a second front bar adjuster that is proximal to the second end of the adjustable front bar.

Still another optional aspect of the present invention provides an apparatus, wherein:
  the adjustable front bar is further comprised of a longitudinal cavity with a cross section configured commensurate with a cross section of the first side bar and the second side bar;
  whereby the first side bar and the second side bar are removably inserted and adjustably secured within the longitudinal cavity for varying a width of the universal frame parallel along a frontal facial plane.

A further optional aspect of the present invention provides an apparatus, wherein:
  the adjustable front bar is further comprised of a nose piece aperture with a cross section configured commensurate with a cross section of the nose piece;
  the nose piece aperture is transverse to the longitudinal cavity of the adjustable front bar, and allows for the adjustment of the height of the nose piece.

Yet a further optional aspect of the present invention provides an apparatus, wherein:
  the nose piece is comprised of:
    a nose piece bar that is removably inserted and adjustably secured within the nose piece aperture for varying of the height of the nose piece; and
    a nose piece arch bar that is coupled with the nose piece bar and substantially configured commensurate with the contour of a human nose.

Still a further optional aspect of the present invention provides an apparatus, wherein:
the first side bar and the second side bar are comprised of:
a fore side bar section parallel to the frontal facial plane;
a first lateral side bar section parallel to a profile facial plane and perpendicular to the frontal facial plane, and coupled with the fore side bar section; and
a second lateral side bar section parallel along the profile facial plane, and parallel to the first lateral side bar section.

Another optional aspect of the present invention provides an apparatus, wherein:
the first lateral side bar section and the second lateral side bar section are comprised of a front and a rear section, with the front section of the first and second lateral side bars integrally coupled with the fore side bar section at a fixed angle; and
the rear section of the first lateral side bar section and the second lateral side bar section is adjustably coupled with a distal ends of the fore sections for allowing the rear sections of first lateral side bar section and the second lateral side bar section to be closed for storage of the universal frame.

Yet another optional aspect of the present invention provides an apparatus, wherein:
the fore side bar section of the first side bar and the second side bar includes a width measuring scale for appropriately setting the width of the universal frame parallel along the frontal facial plane;
the first lateral side bar section of the first side bar and the second side bar includes an anterior-posterior measuring scale for appropriately setting an anterior-posterior displacement of the measuring instrument; and
the first and the second lateral side bar sections of the first side bar and the second side bar include a vertical ear piece having a measuring scale for appropriately setting an ear piece height.

Still another optional aspect of the present invention provides an apparatus, wherein:
the first adjustable ear piece and the second adjustable ear piece are comprised of:
a posterior section configured substantially to comfortably rest on a human ear; and
an anterior section that is substantially straight, which is removeably, coupled, and adjustably secured to the vertical ear piece of the first and second lateral side bar sections.

A further optional aspect of the present invention provides an apparatus, wherein:
the anterior section of the first adjustable ear piece and the second adjustable ear piece further include an anterior-posterior ear piece scale for appropriately setting the anterior-posterior of the first adjustable ear piece and the second adjustable ear piece for accommodating different facial profile sizes.

Yet a further optional aspect of the present invention provides an apparatus, wherein:
the anterior section of the first adjustable ear piece and the second adjustable ear piece is coupled with the vertical ear piece of the first lateral side bar sections and the second lateral side bar sections by an ear piece adjuster.

Still a further optional aspect of the present invention provides an apparatus, wherein:
a first measuring instrument positioner is mounted on the first lateral side bar section of the first side bar, and a second measuring instrument positioner is mounted on the second lateral side bar section of the second side bar;
the first and the second measuring instrument positioners are comprised of a lateral side bar section coupler, and a measuring instrument support carrying bar coupler.

Another optional aspect of the present invention provides an apparatus, wherein:
the lateral side bar section coupler is comprised of a longitudinal through-hole, parallel with the profile facial plane with a cross section configured commensurate with a cross section of the first lateral side bar section and the second lateral side bar section for allowing the measuring instrument positioner to rotate about the first lateral side bar section and the second lateral side bar section, and move longitudinally along the first lateral side bar section and the second lateral side bar section to an anterior-posterior position.

Yet another optional aspect of the present invention provides an apparatus, wherein:
the measuring instrument support carrying bar coupler is comprised of a cavity parallel with the profile facial plane and normal to the longitudinal through-hole with a cross section configured commensurate with a cross section of a measuring instrument support carrying bar for removably inserting, and adjustably securing a measuring instrument at an appropriate height for a patient.

Still another optional aspect of the present invention provides an apparatus, wherein:
the measuring instrument is comprised of one of a contact measuring unit that contacts a corneal apex of an eyeball, and a none contact measuring unit.

A further optional aspect of the present invention provides an apparatus, wherein:
the measuring instrument is comprised of a measuring instrument support carrying bar for removably inserting, and adjustably securing the measuring instrument onto the measuring instrument positioner;
a lateral orbital rim contact base located at one end of the measuring instrument support carrying bar;
a crank bar parallel to the first and the second lateral side bar sections, and coupled with the measuring instrument support carrying bar;
an anterior-posterior measuring instrument adjuster mounted on the crank bar for allowing the anterior-posterior movement of a measuring unit according to a scale.

Another optional aspect of the present invention provides an apparatus, wherein:
the measuring unit is comprised of:
rotateable corneal apex contact arm lever having a distal end that includes a corneal apex contact, and a proximal end having a cross section configured to mount onto the a crank bar.

Yet another optional aspect of the present invention provides an apparatus, wherein:
the measuring unit is comprised of a horizontal base plate mounted onto a crank bar having two vertical plates, which are parallel, with the vertical plates in close proximity to one another to form a slit that is parallel to the first and the second fore side bar sections of the first and the second side bars, enabling an examiner to view a corneal apex through the slit.

Still another optional aspect of the present invention provides an apparatus, wherein:

the measuring unit is comprised of a horizontal base plate mounted onto a crank bar having two vertical pins that are parallel to one another and are aligned along a single plane that is parallel to the first and the second fore side bar sections of the first and the second side bars;

whereby the correct line of sight by an examiner is the observation of a single vertical pin.

A further optional aspect of the present invention provides an apparatus, wherein:

the measuring unit is comprised of sensors coupled onto a crank bar for detecting the corneal apex.

Yet a further optional aspect of the present invention provides an apparatus, wherein:

the sensors are comprised of electronic detecting units that use one of laser, photoelectric, and ultrasound mediums for detection of the corneal apex.

Still a further optional aspect of the present invention provides an apparatus, wherein:

the first and second adjustable earpiece is comprised of an adjustable headband.

Another optional aspect of the present invention provides an apparatus, wherein:

the headband is coupled with an adjustable headpiece.

Yet another optional aspect of the present invention provides an apparatus, wherein:

the scales are digitally displayed.

These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character(s) present corresponding parts throughout:

FIG. 2 is an exemplary perspective illustration of an assembled universal frame and ophthalmic measuring instruments in accordance with the present invention;

FIG. 3B is an exemplary top view illustration of the universal frame and ophthalmic measuring instruments illustrated in FIG. 2 in accordance with the present invention;

FIGS. 4A to 4D are exemplary illustrations of the first embodiment of the ophthalmic measuring instruments illustrated in FIG. 2 in accordance with the present invention;

FIGS. 5A to 5C are exemplary illustrations of the second embodiment of the ophthalmic measuring instruments that may be used with the universal frame illustrated in FIG. 2 in accordance with the present invention;

FIGS. 6A to 6C are exemplary illustrations of the third embodiment of the ophthalmic measuring instruments that may be used with the universal frame illustrated in FIG. 2 in accordance with the present invention;

FIGS. 7A to 7C are exemplary illustrations of the fourth embodiment of the ophthalmic measuring instruments that may be used with the universal frame illustrated in FIG. 2 in accordance with the present invention;

FIGS. 8A to 8C are exemplary illustrations of the fifth embodiment of the ophthalmic measuring instruments that may be used with the universal frame illustrated in FIG. 2 in accordance with the present invention;

FIG. 9 is an exemplary perspective illustration of an automated digital scale display, which can be used with the universal frame and any of the measurement instruments illustrated in FIGS. 2 to 8C in accordance with the present invention;

DETAILED DESCRIPTION OF THE INVENTION

Figure 1A:
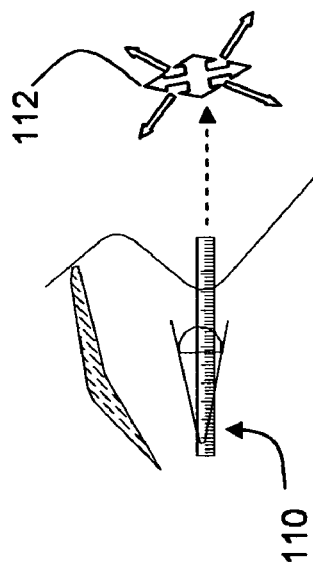
FIG. 1A is an exemplary illustration of the lateral orbital rim and the eyeball.
Figure 1B:
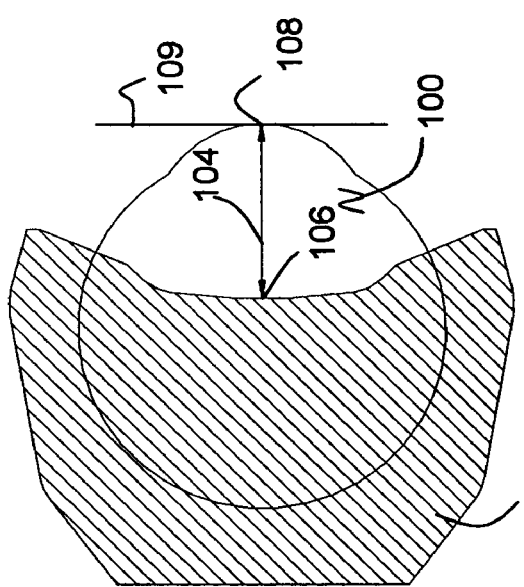
FIG. 1B is an exemplary illustration of prior art ruler used to measure the position of the eyeball along the anterior-posterior positional axis of the eyeball.
Figure 1C:
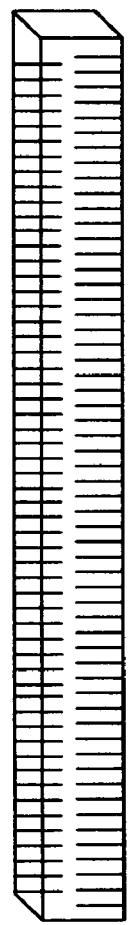
FIG. 1C is an exemplary illustration of a prior art Leudde exopthalmometer.

The present invention provides an opthalmometer that eliminates parallax errors, allows the measuring instrument to be aligned parallel along the anterior-posterior axis of the eye, allows for the proper and independent referencing of each lateral orbital rim by the measuring instrument, and provides for an accurate exopthalmometric and or enopthalmometric measurements. Unlike most prior art, and in particular the HERTEL exopthalmometer, the present invention enables the measuring of each orbital distance 104 independently, thereby eliminating any possible examiner bias. That is, when both orbital distances for both eyes are measured simultaneously (which is done by the HERTEL exopthalmometer), the examiners generally tend to bias (or favor) the measurement of the first or second reading (that may be for the right or the left eye), and adjust the other measurement of the other eye accordingly. The adjustment is usually performed by literally moving the instrument, which obviously distorts the entire measuring process. The present invention provides a universal frame that functions as a stable base for ophthalmic measurements, thereby freeing the hands of an examiner, and includes a measuring instrument detachably mounted or coupled with the universal frame for opthalmometry.

FIG. 2 is an exemplary perspective illustration of an assembled universal frame 200 and ophthalmic measuring instruments 202 and 204 coupled with the universal frame 200 by attachment units 203 and 205, in accordance with the present invention. The universal frame 200 provides for a hands free, stable base for ophthalmic measurements, comprising a first adjustable earpiece 208 and a second adjustable earpiece 210, with measuring instruments 202 and 204 detachably coupled with the universal frame 200 by the attachment units 203 and 205 for exopthalmos and enopthalmos measurements. The universal frame 200 is comprised of an adjustable front bar 212 having an adjustable nosepiece 214, a first side bar 216 coupled with a first end 218 of the adjustable front bar 212, and terminating in the first adjustable earpiece 208. The universal frame 200 further includes a second side bar 220 coupled with a second end 222 of the adjustable front bar 212, and terminating in the second adjustable earpiece 210.

Figure 3A:
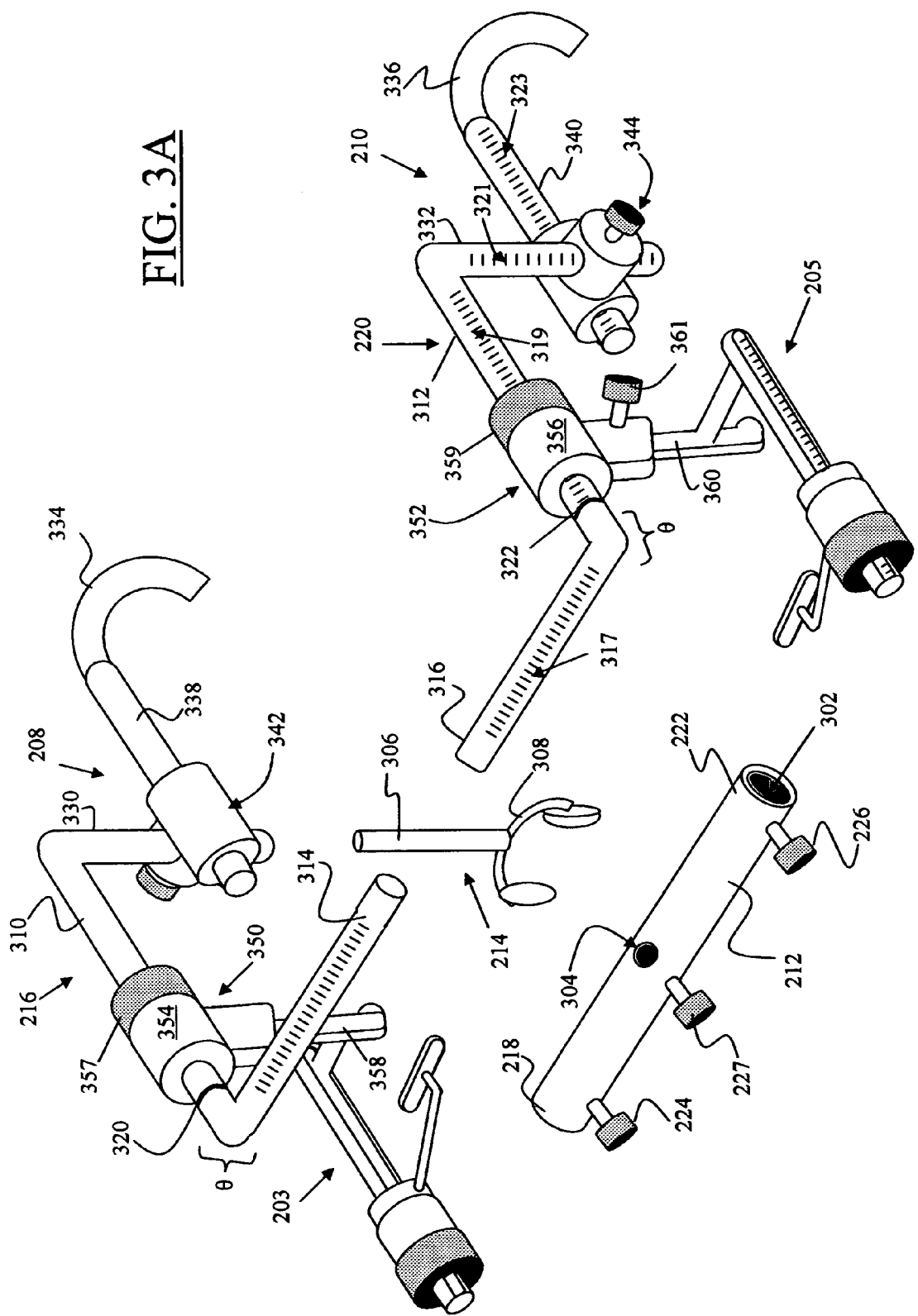
FIG. 3A is an exemplary perspective illustration of the partially disassemble universal frame and ophthalmic measuring instruments illustrated in FIG. 2 in accordance with the present invention.

As further illustrated in FIGS. 2, 3A, and 3B, the adjustable front bar 212 includes a front bar adjuster for varying a width 230 of the universal frame 200 parallel along a frontal facial plane 109. The front bar adjuster is comprised of a first front bar adjuster 224 that is proximal to the first end 218 of the adjustable front bar 212, and a second front bar adjuster 226 that is proximal to the second end 222 of the adjustable front bar 212. Alternatively, the width adjustment mechanism may incorporate an internal mechanism for adjusting the width 230 with notches so that the adjustment is done internally without the need for external adjusters. Any well-known adjustment mechanism may be used to vary the width 230, the length 231, the height 233, or any moving part of the universal frame 200 and the measuring instruments. Non-limiting examples of varying adjustment mechanisms are described, and may include cogwheel, friction, telescopic, etc.

As best illustrated in FIGS. 3A and 3B, the adjustable front bar 212 is further comprised of a longitudinal cavity 302 with a cross section configured commensurate with a cross section of the first side bar 216 and the second side bar 220. This arrangement allows the first side bar 216 and the second side bar 220 to be removably inserted and adjustably secured within the longitudinal cavity 302 for varying the width 230 of the universal frame 200 parallel along a frontal facial plane 109. The adjustable front bar 212 is further comprised of a nosepiece aperture 304 with a cross section configured commensurate with a cross section of the nosepiece bar 306. The nosepiece aperture 304 is transverse to the longitudinal cavity 302 of the adjustable front bar 212, and allows for the adjustment of the height 242 of the nosepiece 214. The nosepiece 214 is comprised of the nosepiece bar 306 that is removably inserted and adjustably secured (by third front bar adjuster 227) within the nosepiece aperture 304 for varying of the height 242 of the nosepiece 214. In addition, the nosepiece 214 further includes a nosepiece arch bar 308 that is coupled with the nosepiece bar 306 and substantially configured commensurate with the contour of a human nose. It should be noted that the nosepiece bar 306 could be curved to configure to the shape of the nose as it protrudes away from the face, and need not be vertically straight, as illustrated.

Referring to FIGS. 2, 3A, and 3B, the first side bar 216 and the second side bar 220 are comprised of a respective fore side bar sections 314 and 316 parallel to the frontal facial plane 109. The first side bar 216 further includes a first lateral side bar section 310 parallel to a profile facial plane and perpendicular to the frontal facial plane 109, and coupled with the first fore side bar section 314. The second side bar 220 includes a second lateral side bar section 312 parallel along the profile facial plane, and parallel to the first lateral side bar section 310, and coupled with the second fore side bar section 316. The fore side bar sections 314 and 316 bent at a fixed angle θ equal to 90°, and couple to the respective first and second lateral side bar sections 310 and 312 through respective well-known hinge mechanisms 320 and 322. That is, the respective first and second lateral side bar sections 310 and 312 are adjustably coupled with the respective fore side bar sections 314 and 316 by the hinge mechanisms 320 and 322 for allowing the first and the second lateral side bar section 310 and 312 to be closed for storage of the universal frame 200, in similar manner to that of conventional spectacles.

The fore side bar sections 314 and 316 include a width measuring scales 317 for appropriately setting the width 230 of the universal frame 200 parallel along the frontal facial plane 109. In addition, the first and second lateral side bar sections 310 and 312 include an anterior-posterior measuring scales 319 for appropriately setting an anterior-posterior displacement 238 of the respective measuring instruments 204 and 202. Further more, the first and the second lateral side bar sections 310 and 312 each, include vertical sections 330 and 332 having measuring scales 321 for appropriately setting the height 232 of the adjustable earpieces 208 and 210.

The first adjustable earpiece 208 and the second adjustable earpiece 210 are comprised of respective posterior sections 334 and 336 configured substantially to comfortably rest on a human ear, and respective anterior sections 338 and 340 that is substantially straight, and removeably coupled, and adjustably secured with the respective vertical sections 330 and 332. The anterior sections 338 and 340 further include an anterior-posterior earpiece scales 323 for appropriately setting the anterior-posterior position 234 of the first and second adjustable earpieces 208 and 210 for accommodating different facial profile sizes.

As illustrated, the anterior sections 338 and 340 are coupled with the respective vertical sections 330 and 332 by respective earpiece adjusters 342 and 344. The earpiece adjusters 342 and 344 are comprised of a first aperture for removeably coupling, and adjustably securing each respective earpiece 208 and 210 by the insertion of the anterior sections 338 and 340 within the first aperture. The earpiece adjusters 342 and 344 are further comprised of a second aperture, which is normal to the first aperture for removeably coupling, and adjustably securing each respective vertical section 330 and 332 within the second aperture. As best illustrated in FIG. 2, the earpiece adjusters 338 and 340 allow anterior-posterior positioning 234, rotational orientation 236, and height adjustment 232 of the earpieces 208 and 210.

As further illustrated in FIGS. 2, 3A, and 3B, the universal frame 200 and the ophthalmic measuring instruments 202 and 204 further include a first measuring instrument positioner 350, which is mounted on the first lateral side bar section 310, and a second measuring instrument positioner 352, which is mounted on the second lateral side bar section 312. The respective first and the second measuring instrument positioners 350 and 352 are comprised of respective lateral side bar section couplers 354 and 356 that allow for anterior-posterior positioning 238 of the first and the second measuring instrument positioners 350 and 352 by adjustment of respective gauging units 357 and 359. As illustrated, postioners 350 and 352 are comprised of a first aperture for removeably coupling, and adjustably securing each onto the respective first and second lateral side bar sections 310 and 312. The postioners 350 and 352 are further comprised of a second aperture, which is normal to the first aperture for removeably coupling, and adjustably securing (by fastener 361 and 363) each respective measuring instrument 202 and 204 within the second aperture. In other words, the lateral side bar section couplers 354 and 356 are comprised of a longitudinal through-hole, parallel with the profile facial plane with a cross section configured commensurate with a cross section of the first and second lateral side bar sections 310 and 312 for allowing the measuring instrument positioners 350 and 352 to rotate 240 about the lateral side bar sections, and move longitudinally 238 along the respective first lateral side bar section 310 and the second lateral side bar section 312 to an anterior-posterior position.

The measuring instrument positioners 350 and 352 are further comprised of a cavity parallel with the profile facial plane and normal to the longitudinal through-hole with a cross section configured commensurate with a cross section of a measuring instrument support carrying bar 358 and 360 of the attachment units 203 and 205 for removably inserting, and adjustably securing measuring instruments 202 and 204 at an appropriate height 244 for a patient. Therefore, as best illustrated in FIG. 2, the postioners 350 and 352 allow anterior-posterior positioning 238, rotational orientation 240, and height adjustment 244 of the measuring instruments 202 and 204. All parameter or scale setting for fixing the positions of the various adjustable components of the universal frame 200 are used for comfortably fitting the universal frame 200 on a patient for examination. In addition, these adjustments may be recorded for future use for determining the progressive condition of the patient when compared with future ophthalmic measurements and examinations. For example, scale 319 can be recorded and used for future measurement following surgical removal of lateral orbital rim. In case of lateral orbital rim fracture, the scale 319 on side may be used as reference for positioning the measuring instrument positioner 350 and 352.

Shown in FIGS. 4A to 8C are exemplary illustrations of various measuring units, including their attachment units 203 and 205 to the universal frame 200. FIGS. 4A to 4D illustrate contact measuring units where a component 422 of the unit contacts the corneal apex 108 of the eyeball 100 (or the eyelid when they are closed) for opthalmic measurements. It should be noted when contacting the eyelid, the thickness of the eyelid must be taken into account. FIGS. 5A to 5C are exemplary illustrations of the various views for a non-contact type mechanical measuring unit, and FIGS. 6A to 8C are exemplary illustrations of non-contact type, electronic measuring units.

Regardless of type of the measuring instrument, all include attachment units 203 and 205 that are comprised of a measuring instrument support carrying bar (358 or 360), hereinafter, simply referenced as 402, for removably inserting, and adjustably securing the measuring instrument (regardless of type) within the measuring instrument positioners 350 and 352. Located at one end of the measuring instrument support carrying bar 402 is a lateral orbital rim contact base 404 that contacts and rests on the orbital rim of the eye socket 102 during examination. At the other end of the bar 402 is a protrusion 406 with a cross section configured to commensurate with the cross section of the measuring instrument positioner cavity (not shown) for removably inserting, and adjustably securing the measuring instruments at an appropriate height for a patient. The protrusion 406 includes a vertical measuring scale 450 for appropriately setting the height of the bar 402 in relation to the frame 200. As further illustrated, the attachment units 203 and 205 further include a crank bar 408 with scales 409 coupled with the measuring instrument support carrying bar 402 by a connector 410. The attachment units 203 and 205 further include an anterior-posterior measuring instrument adjuster 412 mounted on the crank bar 408 for allowing the anterior-posterior movement 430 of a measuring unit. All measuring instruments are coupled with the crank bar 408 by a measuring unit mounting mechanism 414 having a cross section configured to mount onto the crank bar 408, adjacent the measuring instrument adjuster 412, and can move in the orientation 432. It is a well-known general practice that for all globe position measurements the patients generally look straight ahead during the eye exams for accurate measurements.

The contacting measuring unit illustrated in FIGS. 4A to 4D is comprised of a rotateable corneal apex contact arm lever 420 having a distal end that includes a corneal apex contact 422, and is mounted onto the crank bar 408 by the mounting mechanism 414. The contacting measuring unit further includes a washer type element 424 located in between the mounting mechanism 414 and the measuring instrument adjuster 412. During examination, the examiner adjusts the various components of the universal frame 200 for a comfortable and secure fit of the frame on a patient. The measuring instruments 202 and 204 are gradually moved along the orientation 430 towards the patients eyeball 100 by turning the instrument adjuster 412. As the instrument adjuster 412 is turned, the corneal apex contact arm lever 420 is moved towards the eyeball 100, along the orientation 430. The examiner can adjust the arm lever 420 along the orientation 432, or the measuring instrument positioners 350 and 352 along the orientations 238, 240 or 244 for positioning the corneal apex contact 422 against the cornea of the eye (or the eyelid when the eyelids are closed). The actual contact unit 422 may also move in the orientation 433. Measurement readings can be taken from the scales on the universal frame 200 and the attachment units 203 and 205 to determine the extent of exopthalmos or the enopthalmos conditions. It should be noted that when measurements are taken from the eyelids, the thickness of the eyelids must be taken into account.

FIGS. 5A to 5C are exemplary illustrations of different views for a non-contacting measuring unit, which is comprised of a horizontal base plate 502 mounted onto a crank bar 408 by the mounting mechanism 414 having two vertical pins 504 and 506 that are parallel to one another and are aligned along a single plane (the vertical frontal facial plane 109). During examination, the correct line of sight by an examiner is the observation of the corneal apex 108, when both pins are aligned and perceived or viewed as a single vertical pin. In other words, the examiner correctly views the apex of the cornea when the pins are tangent therewith, and are perceived as one. The concept is to align two elements along the corneal apex such that the two elements are perceived as one.

As an alternative embodiment to the pins, a non-contacting measuring unit may comprise of horizontal base plate 502 mounted onto a crank bar 408 by a mounting mechanism 414, with the non-contacting measuring unit having two vertical plates (instead of pins), which are parallel to one another, with the vertical plates in close proximity to one another to form a slit, enabling an examiner to view the corneal apex 108 through the slit. A correct viewing is achieved when the apex of the cornea appears within the narrow slit.

FIGS. 6A to 8C are exemplary illustrations of non-contact type, electronic measuring units. FIGS. 6A to 6C are exemplary illustrations of the various views for an electronic non-contact type measuring unit, having a component 602 functioning as an illuminating pointer. FIGS. 7A to 7C are exemplary illustrations of the various views for an electronic non-contact type measuring unit, which includes a reflective detection mechanism, and FIGS. 8A to 8C are exemplary illustrations of non-contact type, electronic measuring units that measure distance. All non-contacting electronic measuring units are coupled onto a crank bar for detecting the corneal apex.

FIGS. 6A to 6C are exemplary illustrations of the various views for the electronic non-contact type measuring unit, which includes the component 602 that functions to generate a beam of light, which is pointed towards the nose section of the patient, parallel along the vertical frontal facial plane 109. A non-limiting exemplary component 602 may include a laser pointer device, which is well-known. During examination, the examiner adjusts the various components of the universal frame 200 for a comfortable and secure fit of the frame 200 on a patient. The measuring instruments 202 and 204 are gradually moved along the orientation 430 towards the patients eyeball 100 by turning the instrument adjuster 412. As the instrument adjuster 412 is turned, the light beam emanated from the component 602 is moved towards the eyeball 100, along the orientation 430, parallel to the frontal facial plane 109. Measurement readings can be taken when the beam of light emanated from the component 602 is interrupted by the corneal apex. These measurements can be taken from the scales on the universal frame 200 and the attachment units 203 and 205 to determine the extent of exopthalmos or the enopthalmos conditions. It should be noted that a single beam, a plurality thereof, or a flat beam (a two dimensional beam of light with length and width) may be used, with the plurality of beams or the flat beam being oriented parallel aligned along the vertical facial plane 109. The single, plural or flat light beams are well-known in the art.

FIGS. 7A to 7C are exemplary illustrations of the various views for the electronic non-contact type measuring unit, which includes the component 702 that functions as a transceiver sensor to detect the cornea apex. That is, the component 702 transmits a signal (light, ultra-sound, etc.), which impinges upon the corneal apex as the adjuster mechanism 412 is moved to move the measuring unit toward the eyeball 100. That is, as the instrument adjuster 412 is turned, the signal emanated from the component 702 is moved towards the eyeball 100, along the orientation 430, parallel to the frontal facial plane 109. Upon contact with the corneal apex, the transmitted signal is then reflected back to the component 702, where it is received, generating either a sound or activating one or both of the indicator lights 706 and 708, informing the user that the corneal apex has been detected. The switch 704 is the ON/OFF switch, and the indicator light 706 is the optic detection indicator, and indicator light 708 is power ON indicator. The illustrated wire or cable 710 is a power cable. The component 702 is well-known, and is made by many different manufactures, including Banner®.

FIGS. 8A to 8C are exemplary illustrations of the various views for the electronic non-contact type measuring unit, which includes the component 802 that functions as a transceiver sensor to detect the amount of distance between the cornea apex and the actual surface area of the sensor facing the corneal apex. This distance may be used to calculate and determine the extent of exopthalmos or the enopthalmos conditions. As well be apparent to those skilled in the art, before any measurements are taken, the component 802 may be adjusted in orientations 432 and 840 for accurate readings, with the orientation 840 allowing the instrument to move along the coupler 810. As illustrated, the component 802 transmits a signal (light, ultra-sound, etc.), which directly impinges upon the corneal apex, perpendicular to the frontal facial plane 109. Upon contact with the corneal apex, the transmitted signal is then reflected back to the component 802, where it is received, indicating the distance between the component 802 and that of the corneal apex. The measured distance is then subtracted by the indicated length on the crank bar 408 to determine the extent of exopthalmos or the enopthalmos conditions, and displayed on the display unit 804 as digital characters 814. Optionally, the display unit 804 and the component 802 may be integral, not requiring the connecting communication cable 806, and further, the component 802 may be fixed onto the crank bar 408, and not moved. The measuring instrument 802 may be powered by a source via a cable 812.

FIG. 9 is an exemplary perspective illustration of an automated digital scale display, which can be used with any of the measurement instruments and the frame illustrated in FIGS. 2 to 8C. The measuring instrument and its corresponding connections include similar corresponding or equivalent components as the other measuring instruments that are shown in FIGS. 2 to 8C, and described above. Therefore, for the sake of brevity, clarity, convenience, and to avoid duplication, the general description of FIG. 9 will not repeat every corresponding or equivalent component that has already been described above in relation to measuring instruments that are shown in FIGS. 2 to 8C.

As is illustrated in FIG. 9, instead of using the scales 409 on the crank arm 408, a digital scale display 904 may be provided that displays the measured movement of the measuring instrument along the orientation 430. In other words, the display unit 904 may be used as part of the overall measurement scheme instead of the scales 409 on the crank arm 408. The scale display unit 904 is well-known in the art, and uses the same technology as used in well-known digital caliper instruments. In fact, an analog dial version may be used, however, the digital is preferable.

Figure 10A:
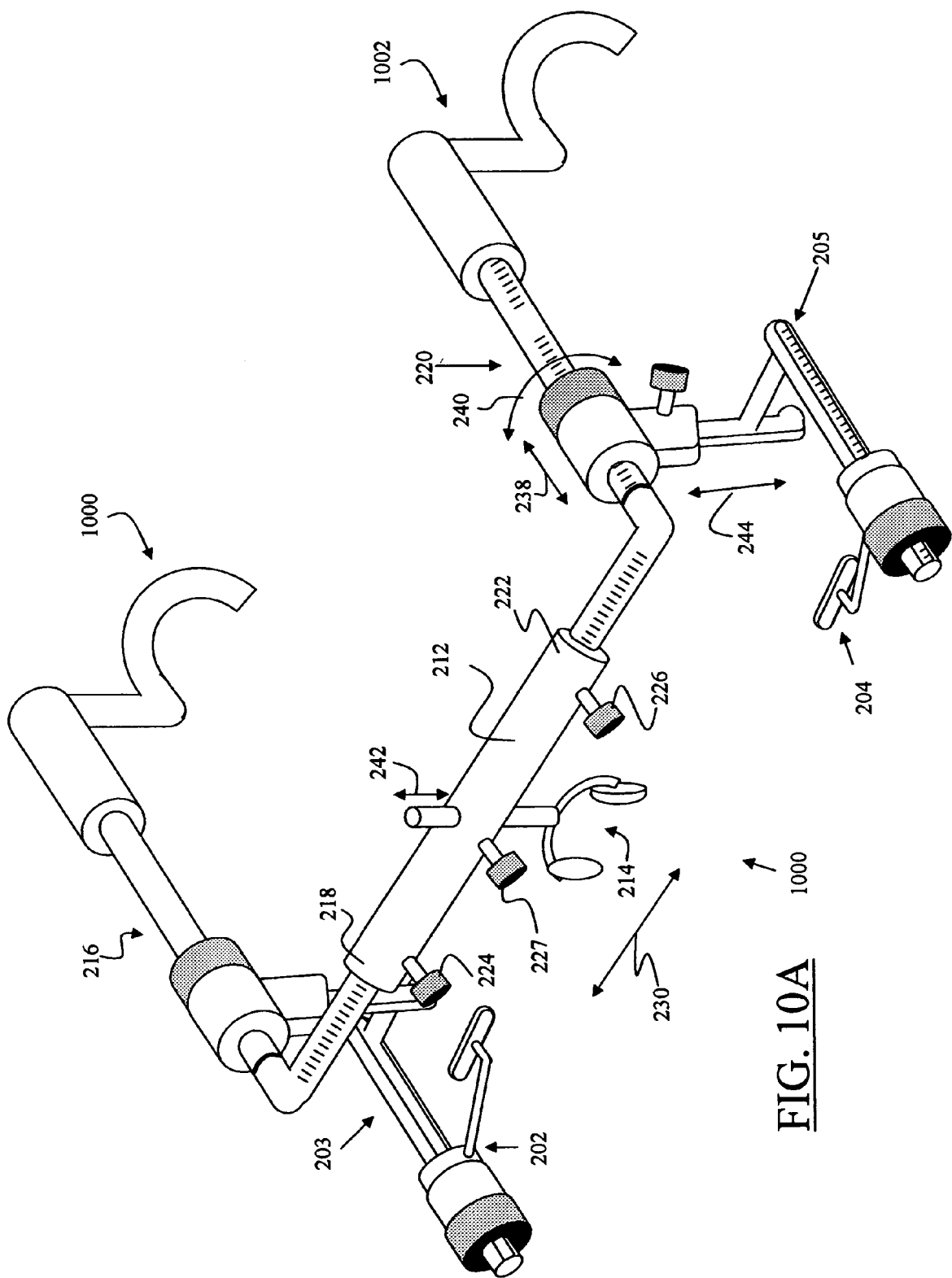
FIG. 10A is an exemplary perspective view illustration of another embodiment for an universal frame with further illustration of exemplary ophthalmic measuring instruments in accordance with the present invention.
Figure 10B:
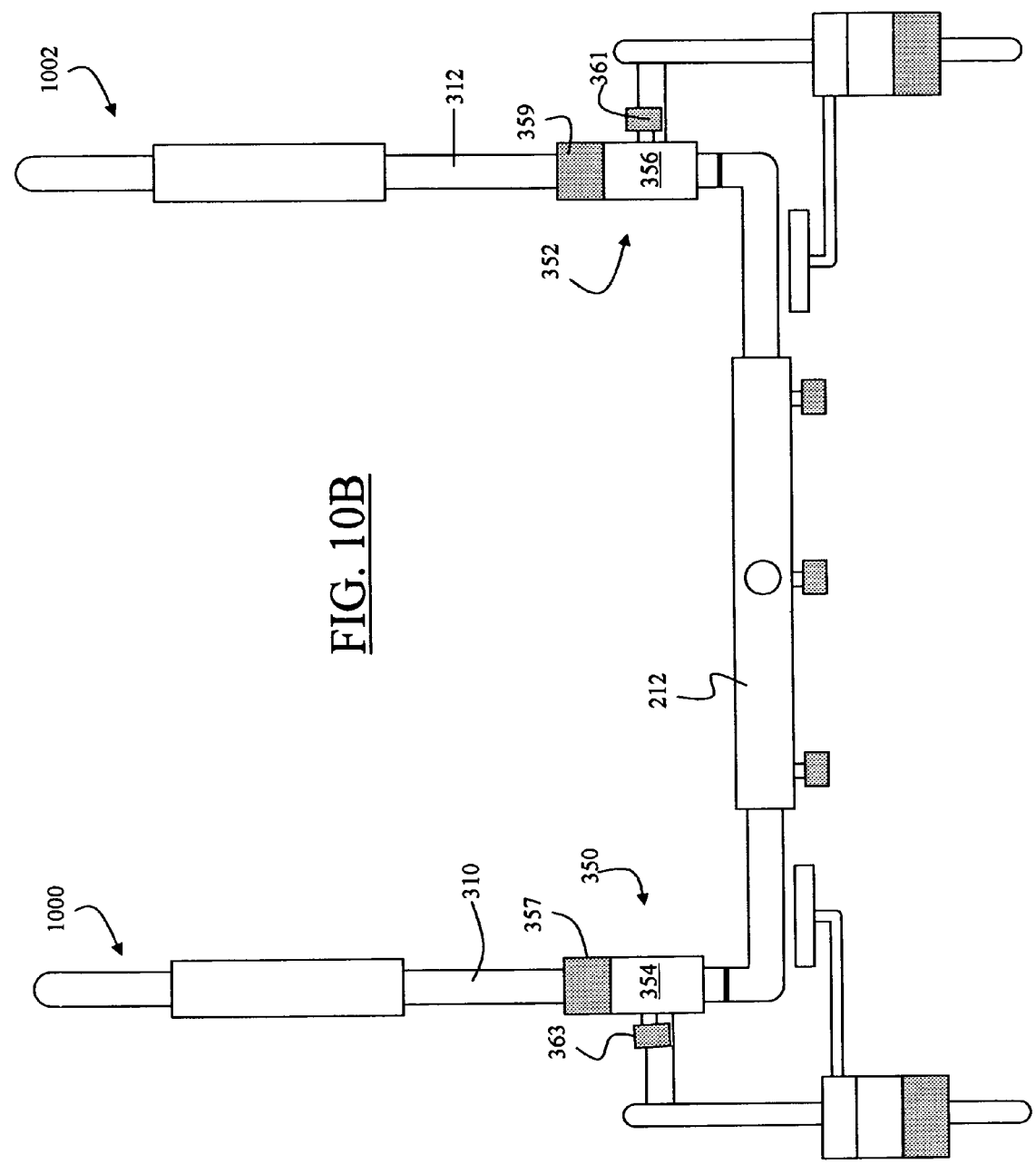
FIG. 10B is an exemplary top view illustration of the universal frame illustrated in FIG. 10A in accordance with the present invention.

FIG. 10A is an exemplary perspective view illustration of another embodiment for an universal frame with an exemplary ophthalmic measuring instrument in accordance with the present invention, and FIG. 10B is an exemplary top view illustration of the universal frame illustrated in FIG. 10A. The universal frame 1000 includes similar corresponding or equivalent components as the universal frame 200 that is shown in FIGS. 2 to 9, and described above. Therefore, for the sake of brevity, clarity, convenience, and to avoid duplication, the general description of FIGS. 10A and 10B will not repeat every corresponding or equivalent component that has already been described above in relation to universal frame 200 that is shown in FIGS. 2 to 9. As illustrated in FIGS. 10A and 10B the a major difference between the universal frame 200 and that of 1000 is that the height 232 of the universal frame 1000 is fixed, and the adjustment of the ear pieces and their movement 234 may be achieved by a variety of methods, non-limiting examples of which may include cogwheel, friction, telescopic, etc.

Figure 11A:
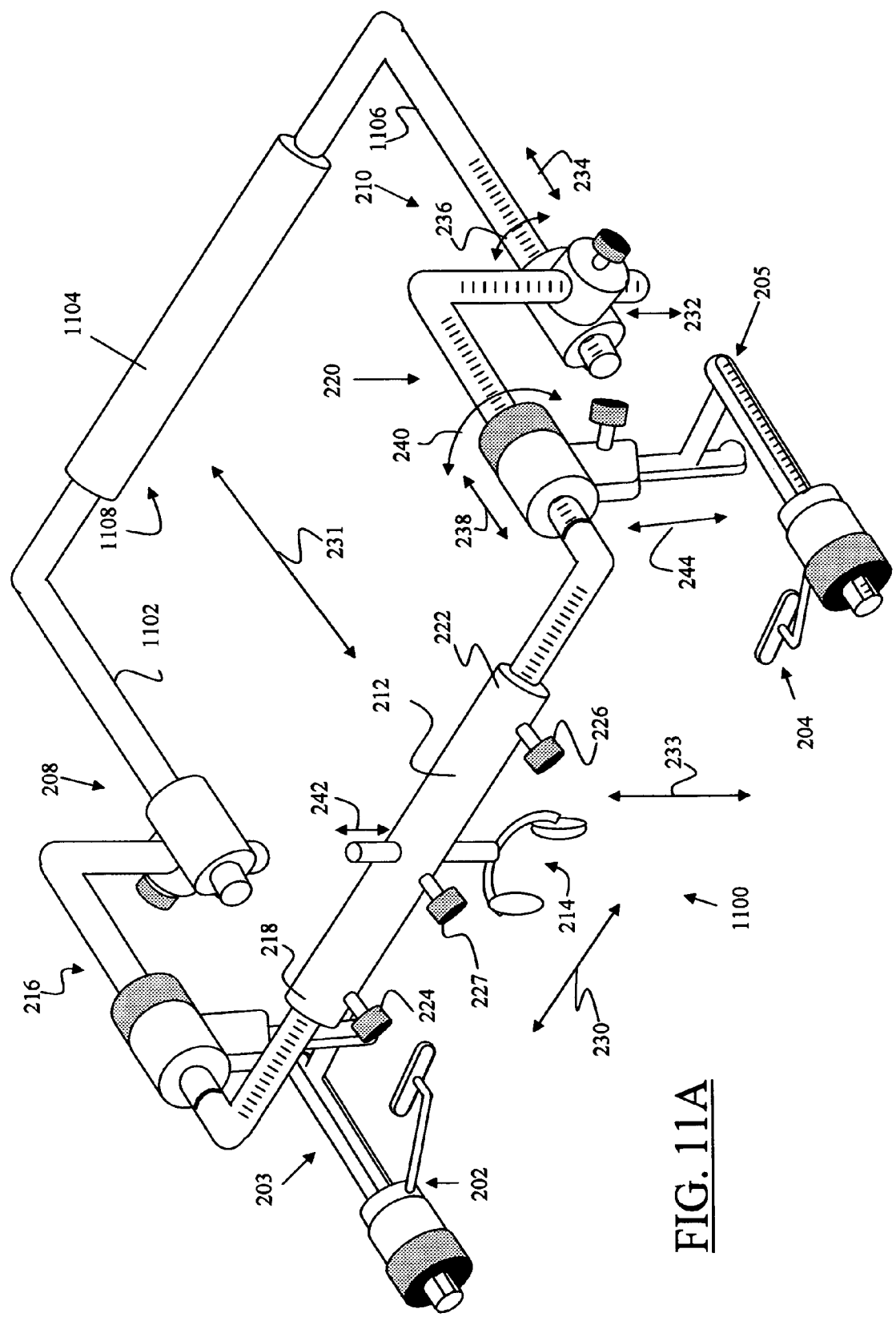
FIG. 11A is an exemplary perspective view illustration of yet another embodiment for an universal frame with further illustration of exemplary ophthalmic measuring instruments in accordance with the present invention.
Figure 11B:
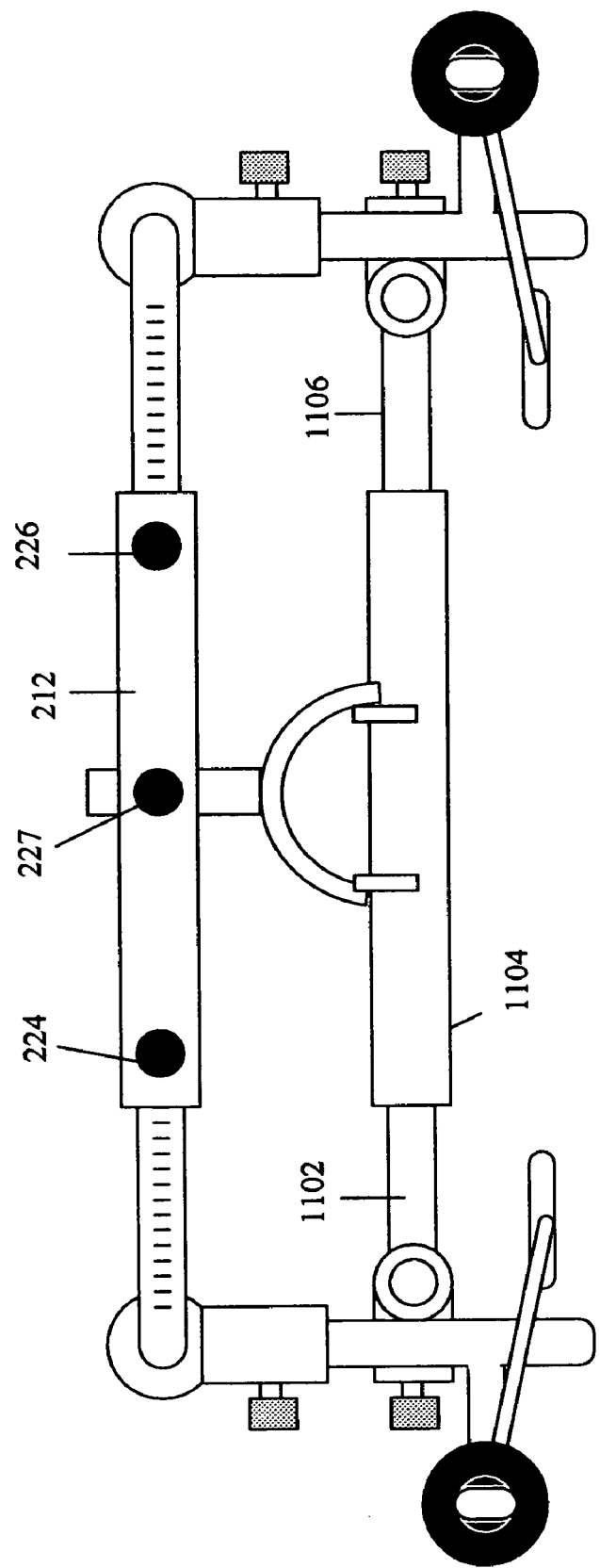
FIG. 11B is an exemplary front view illustration of the universal frame illustrated in FIG. 11A in accordance with the present invention.
Figure 11C:
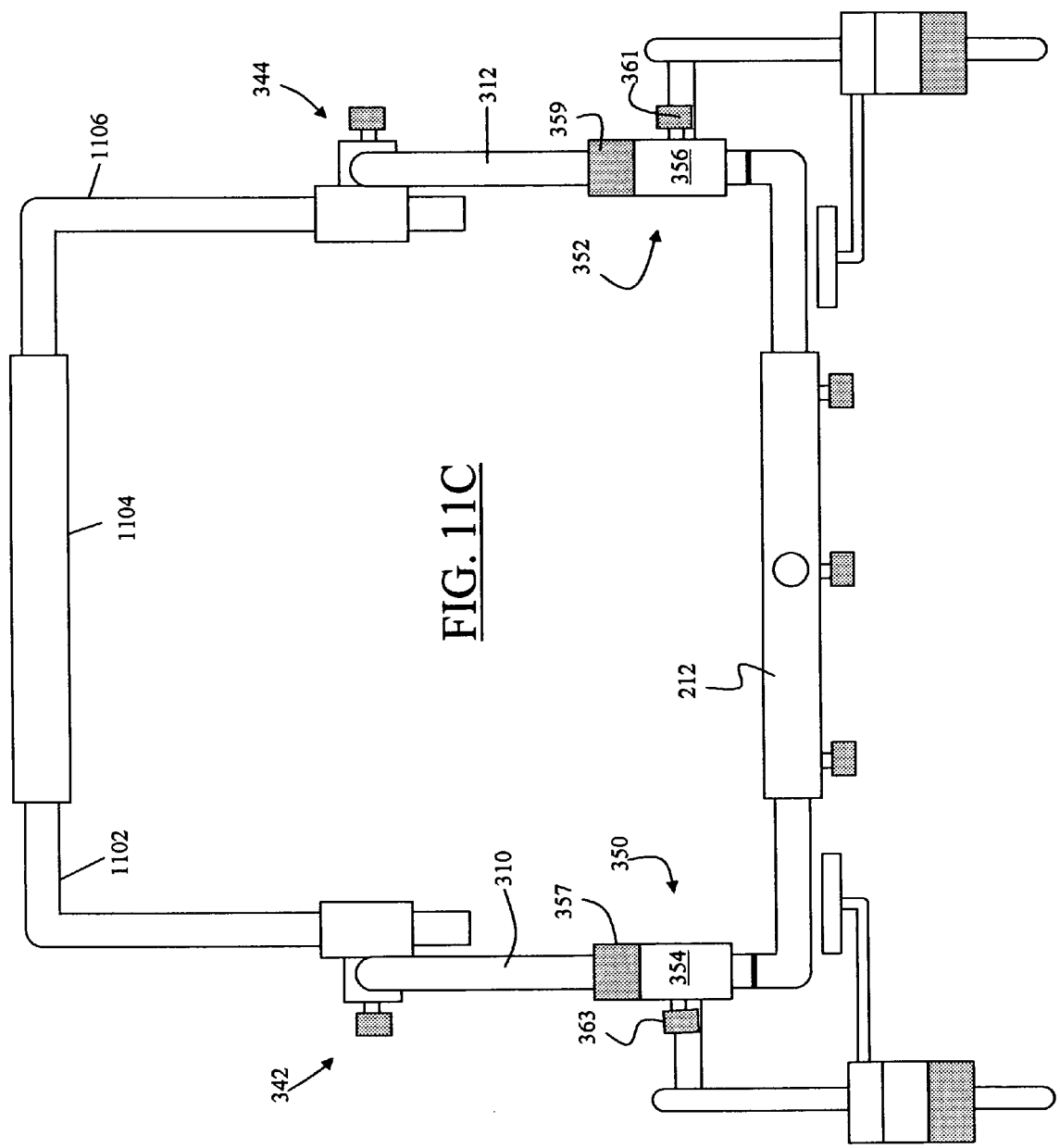
FIG. 11C is an exemplary top view illustration of the universal frame illustrated in FIG. 11A in accordance with the present invention.

FIG. 11A is an exemplary perspective view illustration of another embodiment for an universal frame 1100 having an adjustable headband 1108 with an exemplary ophthalmic measuring instrument in accordance with the present invention, and FIGS. 11B and 11C are exemplary side, front, and top view illustration of the universal frame 1100 illustrated in FIG. 10A. The universal frame 1100 includes similar corresponding or equivalent components as the universal frames 200 and 1000 that are shown in FIGS. 2 to 10B, and described above. Therefore, for the sake of brevity, clarity, convenience, and to avoid duplication, the general description of FIGS. 11A to 11C will not repeat every corresponding or equivalent component that has already been described above in relation to universal frames 200 and 1000 that are shown in FIGS. 2 to 10.

As illustrated in FIG. 11A, the construction of the adjustable headband 1108 is similar to the construction of the front section of the frame in that the adjustable headband 1108 is comprised of a an adjustable headband bar 1104 varying a width 230 of the universal frame 1100 parallel along a frontal facial plane 109. The adjustable headband bar 1104 is comprised of a longitudinal cavity (not shown) with a cross section configured commensurate with a cross section of the first headband side bar 1102 and the second headband side bar 1106. This arrangement allows the first headband side bar 1102 and the second headband side bar 1106 to be removably inserted and adjustably secured within the longitudinal cavity for varying the width 230 of the universal frame 1100 parallel along a frontal facial plane 109.

Figure 12:
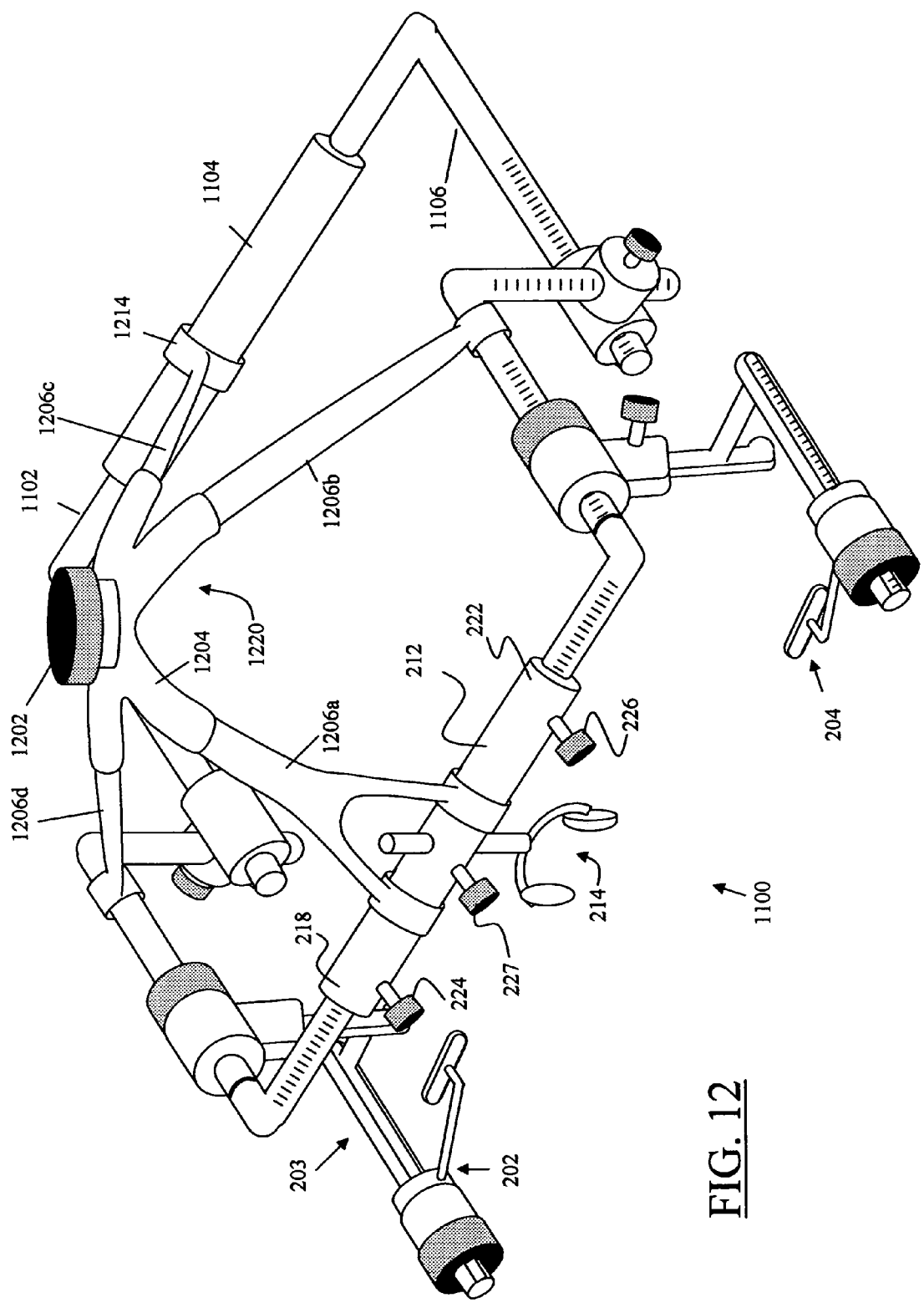
FIG. 12 is an exemplary perspective view illustration of still a further embodiment for an universal frame with further illustration of exemplary ophthalmic measuring instruments in accordance with the present invention that uses a headpiece.

FIG. 12 is an exemplary perspective view illustration of another embodiment for an universal frame 1200 having an adjustable headband 1108, including an adjustable headpiece 1220 with an exemplary ophthalmic measuring instrument in accordance with the present invention. The universal frame 1200 includes similar corresponding or equivalent components as the universal frames 200, 1000, and 1100 that are shown in FIGS. 2 to 11C, and described above. Therefore, for the sake of brevity, clarity, convenience, and to avoid duplication, the general description of FIG. 12 will not repeat every corresponding or equivalent component that has already been described above in relation to universal frames 200, 1000, and 1100 that are shown in FIGS. 2 to 11C.

As illustrated in FIG. 12, the adjustable headpiece 1220 facilitates the raising or lowering of the entire frame 1200 for a more comfortable fit of the frame 1200 on the head of the patient. That is, it allows for a more secure positioning of the frame 1200 on the head of the patient. The adjustable headpiece 1220 can change the vertical (up and down) position of the frame 1200 in relation to the head of the patient by the adjusting knob 1202, which when rotated clockwise or counterclockwise, will move the frame 1200 in a vertical direction in relation to the head. The rotation of the adjusting knob 1202 will pull-in or push-out the illustrated arms 1206 (*a, b, c,* and *d*) towards or away from the cover 1204 for moving the frame 1200 vertically up or vertically down. It should be noted that although four arms 1206 (*a, b, c,* and *d*) are illustrated, the same functionality can be accomplished using only two arms 1206 that are in opposite directions, for example, (1206*a* and 1206*c*) or (1206*b* and 1206*d*).

Although the invention has been described in considerable detail in language specific to structural features and or method acts, it is to be understood that the invention defined in the appended claims is not necessarily limited to the specific features or acts described. Rather, the specific features and acts are disclosed as preferred forms of implementing the claimed invention. Therefore, while exemplary illustrative embodiments of the invention have been described, numerous variations and alternative embodiments will occur to those skilled in the art. For example, although the instrument of the present invention is mainly described in relation to the measurement of the anterior-posterior axial position of the eyeball using the lateral orbital rim as the reference, it would be apparent to those skilled in the art to modify and use the universal frame as the stabilizing base to measure the degree of exophthalmia using the superior and inferior orbital rims as the reference points. In addition, any well-known adjustment mechanism may be used to vary orientations or directions of any moving or adjustable component of the present invention, including the universal frame and the measuring instruments. Furthermore, it should further be noted that all mechanical scales on the universal frame or the measuring units may be replaced by well-known internal or external electronic calibration or measuring systems that may be used for the reading of the extent of exopthalmos or the enopthalmos conditions. Stated otherwise, for example, the scales 409 on bar 408 may be replaced by electronic scales that detect and display the desired scale electronically, via a small exemplary Liquid Crystal Display (LCD) display unit. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, proximal, distal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

What is claimed is:

1. An apparatus, comprising:
   a universal frame for providing a hands free, stable base for ophthalmic measurements comprising a first adjustable ear piece and a second adjustable ear piece; and
   a measuring instrument detachably connected with the universal frame for exopthalmos and enopthalmos measurements.

2. The apparatus of claim 1, wherein:
   the universal frame is comprised of:
      an adjustable front bar having an adjustable nose piece;
      a first side bar coupled with a first end of the adjustable front bar, and terminating in the first adjustable ear piece;
      a second side bar coupled with a second end of the adjustable front bar, and terminating in the second adjustable ear piece.

3. The apparatus of claim 2, wherein:
   the adjustable front bar includes a front bar adjuster for varying a width of the universal frame parallel along a frontal facial plane.

4. The apparatus of claim 3, wherein:
   the front bar adjuster is comprised of:
      a first front bar adjuster that is proximal to the first end of the adjustable front bar; and
      a second front bar adjuster that is proximal to the second end of the adjustable front bar.

5. The apparatus of claim 2, wherein:
the adjustable front bar is further comprised of a longitudinal cavity with a cross section configured commensurate with a cross section of the first side bar and the second side bar;
whereby the first side bar and the second side bar are removably inserted and adjustably secured within the longitudinal cavity for varying a width of the universal frame parallel along a frontal facial plane.

6. The apparatus of claim 2, wherein:
the adjustable front bar is further comprised of a nose piece aperture with a cross section configured commensurate with a cross section of the nose piece;
the nose piece aperture is transverse to the longitudinal cavity of the adjustable front bar, and allows for the adjustment of the height of the nose piece.

7. The apparatus of claim 6, wherein:
the nose piece is comprised of:
a nose piece bar that is removably inserted and adjustably secured within the nose piece aperture for varying of the height of the nose piece; and
a nose piece arch bar that is coupled with the nose piece bar and substantially configured commensurate with the contour of a human nose.

8. The apparatus of claim 2, wherein:
the first side bar and the second side bar are comprised of:
a fore side bar section parallel to the frontal facial plane;
a first lateral side bar section parallel to a profile facial plane and perpendicular to the frontal facial plane, and coupled with the fore side bar section; and
a second lateral side bar section parallel along the profile facial plane, and parallel to the first lateral side bar section.

9. The apparatus of claim 8, wherein:
the first lateral side bar section and the second lateral side bar section are comprised of a front and a rear section, with the front section of the first and second lateral side bars integrally coupled with the fore side bar section at a fixed angle; and
the rear section of the first lateral side bar section and the second lateral side bar section is adjustably coupled with a distal ends of the fore sections for allowing the rear sections of first lateral side bar section and the second lateral side bar section to be closed for storage of the universal frame.

10. The apparatus of claim 8, wherein:
the fore side bar section of the first side bar and the second side bar includes a width measuring scale for appropriately setting the width of the universal frame parallel along the frontal facial plane;
the first lateral side bar section of the first side bar and the second side bar includes an anterior-posterior measuring scale for appropriately setting an anterior-posterior displacement of the measuring instrument; and
the first and the second lateral side bar sections of the first side bar and the second side bar include a vertical ear piece having a measuring scale for appropriately setting an ear piece height.

11. The apparatus of claim 10, wherein:
the measuring scale is a digital display scale.

12. The apparatus of claim 8, wherein:
a first measuring instrument positioner is mounted on the first lateral side bar section of the first side bar, and a second measuring instrument positioner is mounted on the second lateral side bar section of the second side bar;
the first and the second measuring instrument positioners are comprised of a lateral side bar section coupler, and a measuring instrument support carrying bar coupler.

13. The apparatus of claim 12, wherein:
the lateral side bar section coupler is comprised of a longitudinal through-hole, parallel with the profile facial plane with a cross section configured commensurate with a cross section of the first lateral side bar section and the second lateral side bar section for allowing the measuring instrument positioner to rotate about the first lateral side bar section and the second lateral side bar section, and move longitudinally along the first lateral side bar section and the second lateral side bar section to an anterior-posterior position.

14. The apparatus of claim 12, wherein:
the measuring instrument support carrying bar coupler is comprised of a cavity parallel with the profile facial plane and normal to the longitudinal through-hole with a cross section configured commensurate with a cross section of a measuring instrument support carrying bar for removably inserting, and adjustably securing a measuring instrument at an appropriate height for a patient.

15. The apparatus of claim 8, wherein:
the measuring instrument is comprised of a measuring instrument support carrying bar for removably inserting, and adjustably securing the measuring instrument onto a measuring instrument positioner;
a lateral orbital rim contact base located at one end of the measuring instrument support carrying bar;
a crank bar parallel to the first and the second lateral side bar sections, and coupled with the measuring instrument support carrying bar;
an anterior-posterior measuring instrument adjuster mounted on the crank bar for allowing a anterior-posterior movement of a measuring unit according to a scale.

16. The apparatus of claim 15, wherein:
the measuring scale is a digital display scale.

17. The apparatus of claim 15, wherein:
the measuring unit is comprised of:
rotateable corneal apex contact arm lever having a distal end that includes a corneal apex contact, and a proximal end having a cross section configured to mount onto the a crank bar.

18. The apparatus of claim 15, wherein:
the measuring unit is comprised of a horizontal base plate mounted onto the crank bar having two vertical plates, which are parallel, with the vertical plates in close proximity to one another to form a slit that is parallel to the first and the second fore side bar sections of the first and the second side bars, enabling an examiner to view a corneal apex through the slit.

19. The apparatus of claim 15, wherein:
the measuring unit is comprised of a horizontal base plate mounted onto the crank bar having two vertical pins that are parallel to one another and are aligned along a single plane that is parallel to the first and the second fore side bar sections of the first and the second side bars;
whereby the correct line of sight by an examiner is the observation of a single vertical pin.

20. The apparatus of claim 15, wherein:
the measuring unit is comprised of sensors coupled onto a crank bar for detecting the corneal apex.

21. The apparatus of claim 20, wherein:

the sensors are comprised of electronic detecting units that use one of laser, photoelectric, and ultrasound mediums for detection of the corneal apex.

22. The apparatus of claim 1, wherein:

the first adjustable ear piece and the second adjustable ear piece are comprised of:

a posterior section configured substantially to comfortably rest on a human ear; and an anterior section that is substantially straight, which is removeably, coupled, and adjustably secured to the vertical ear piece of the first and second lateral side bar sections.

23. The apparatus of claim 22, wherein:

the anterior section of the first adjustable ear piece and the second adjustable ear piece further include an anterior-posterior ear piece scale for appropriately setting the anterior-posterior of the first adjustable ear piece and the second adjustable ear piece for accommodating different facial profile sizes.

24. The apparatus of claim 23, wherein:

the measuring scale is a digital display scale.

25. The apparatus of claim 22, wherein:

the anterior section of the first adjustable ear piece and the second adjustable ear piece is coupled with the vertical ear piece of the first lateral side bar sections and the second lateral side bar sections by an ear piece adjuster.

26. The apparatus of claim 22, wherein:

the anterior section of the first adjustable ear piece and the second adjustable ear piece is coupled with the horizontal ear piece of the first lateral side bar sections and the second lateral side bar sections by an ear piece adjuster.

27. The apparatus of claim 1, wherein:

the measuring instrument is comprised of one of a contact measuring unit that contacts a corneal apex of an eyeball, and a none contact measuring unit.

28. The apparatus of claim 1, wherein:

the first and second adjustable earpiece is comprised of an adjustable headband.

29. The apparatus of claim 28, wherein:

the headband is coupled with an adjustable headpiece.

30. The apparatus of claim 1, wherein:

the universal frame includes electronic digital scales.

* * * * *